(12) United States Patent
Pollack et al.

(10) Patent No.: US 10,206,900 B2
(45) Date of Patent: Feb. 19, 2019

(54) TREATMENTS FOR FIBROTIC DISEASES

(71) Applicant: MOR RESEARCH APPLICATIONS LTD., Tel Aviv (IL)

(72) Inventors: Ayala Pollack, Rehovot (IL); Zeev Dvashi, Kiryat Ono (IL)

(73) Assignee: Mor Research Applications Ltd., Tel Aviv (IL)

( * ) Notice: Subject to any disclaimer, the term of this patent is extended or adjusted under 35 U.S.C. 154(b) by 0 days.

(21) Appl. No.: 15/083,370

(22) Filed: Mar. 29, 2016

(65) Prior Publication Data

US 2016/0206591 A1 Jul. 21, 2016

Related U.S. Application Data

(63) Continuation-in-part of application No. PCT/IL2014/050882, filed on Oct. 7, 2014.

(60) Provisional application No. 61/887,747, filed on Oct. 7, 2013, provisional application No. 62/139,761, filed on Mar. 29, 2015.

(51) Int. Cl.
*A61K 31/335* (2006.01)
*C07K 16/40* (2006.01)

(52) U.S. Cl.
CPC ............ *A61K 31/335* (2013.01); *C07K 16/40* (2013.01)

(58) Field of Classification Search
CPC .............................. A61K 31/335; C07K 16/40
USPC ...................................................... 558/408
See application file for complete search history.

(56) References Cited

U.S. PATENT DOCUMENTS

2013/0150422 A1* 6/2013 Rotin .................. C07D 313/00
514/414

FOREIGN PATENT DOCUMENTS

WO 02/48135 6/2002
WO 03/097615 11/2003

OTHER PUBLICATIONS

Strippoli et al., PLOS One (2012), 7(2), e31492, 12 pages.*
Brady et al. 2017,https://www.reviewofophthalmology.com/article/pyr-an-update-on-prevention-management.*
Ma et al., 2011, American Journal of Physiology, 300 (6, Pt. 2), F1410-F1421.*
CrohnsDiseasePrevention, 2017, https://www.webmd.com/ibd-crohns-disease/crohns-disease/tc/crohns-disease-prevention.*
CirrhosisPrevention, 2017, http://www.chiro.org/nutrition/FULL/Can_Cirrhosis_Be_Prevented.shtml.*
CysticFibrosisPrevention, 2017, https://www.webmd.com/children/tc/cystic-fibrosis-prevention.*
Fibrosis, 2017, https://en.wikipedia.org/wiki/Fibrosis.*
Takahashi et al., Investigative Ophthalmology & Visual Science (2015), 56(4), 2449-2458.*
Takahashi E et al, Tumor necrosis factor-alpha regulates transforming growth factor-beta-dependent epithelial-mesenchymal transition by promoting hyaluronan-CD44-moesin interaction, JBC:285, 4060-4073, 2009.
Strippoli R, Benedicto I, Perez Lozno ML, Pellinen T, Sandoval P, et al. (2012) Inhibition of Transforming Growth Factor-Activated Kinase 1 (TAK1) Blocksand Reverses Epithelial to Mesenchymal Transition of Mesothelial Cells. PLoS ONE 7(2): e31492. doi:10.1371/journal.pone.0031492.
Gardner A et al, "The critical role of TAK1 in accentuated epithelial to mesenchymal transition in obliterative bronchiolitis after lung transplantation" Am J. Path, 180:2293-2306, 2012.
Ninomiya-Tsuji et al."A Resorcylic Acid Lactone, 5Z-7-Oxozeaenol, Prevents Inflammation by Inhibiting the Catalytic Activity of TAK1 MAPK Kinase Kinase" JBC, 278: 18485-18490, 2003.
Broglie et al "Transforming Growth Factor beta-activated Kinase 1 (TAK1) Kinase Adaptor, TAK1-binding Protein 2, Plays Dual Roles in TAK1 Signaling by Recruiting Both an Activator and an Inhibitor of TAK1 Kinase in Tumor Necrosis Factor Signaling Pathway" JBC, 285:2333-2339, 2010.
Inoue et al "Maxacalcitol ameliorates tubulointerstitial fibrosis in obstructed kidneys by recruiting PPM1A/VDR complex to pSmad3" Lab Invest, 92:1686-1687, 2012.

* cited by examiner

*Primary Examiner* — Sun Jae Yoo
(74) *Attorney, Agent, or Firm* — JMB Davis Ben-David

(57) ABSTRACT

Disclosed herein are methods for treatment for fibrosis, ocular pathologies associated with fibrosis, including proliferative vitreoretinopathy (PVR) by inhibiting the activity of activated transforming growth factor β activated kinase 1 (TAK1), or activation thereof. Pharmaceutical compositions for use in the described treatments are also provided.

3 Claims, 19 Drawing Sheets
(8 of 19 Drawing Sheet(s) Filed in Color)

5Z-7 oxozeaenol    −            +

Full medium    +            +

Figure 6A
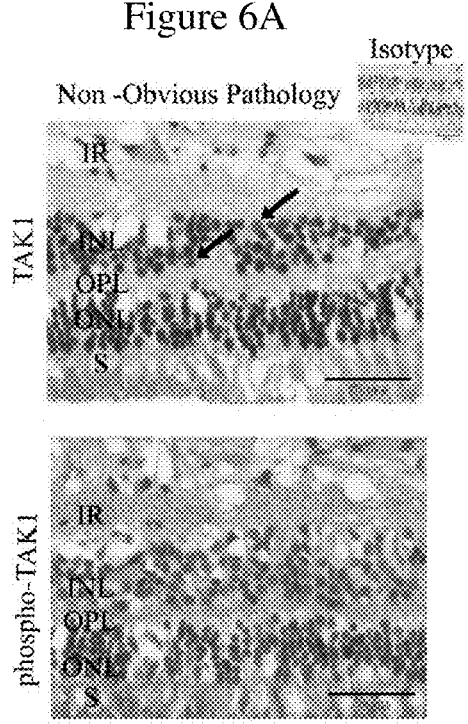
Figure 6C
Figure 6B
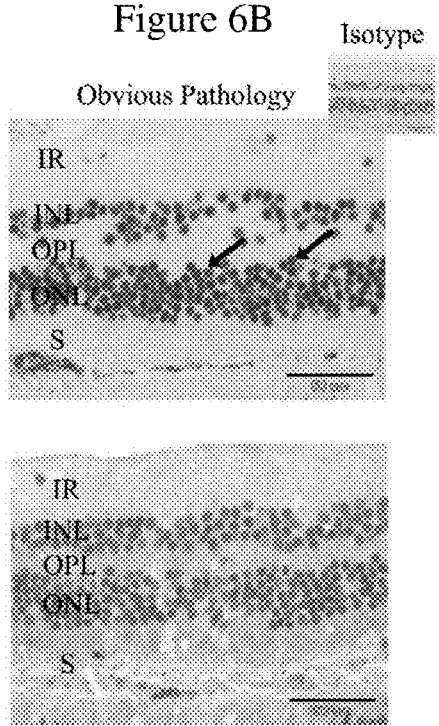
Figure 6D

Figure 7A
Figure 7B
Non-Obvious Pathology
Obvious Pathology
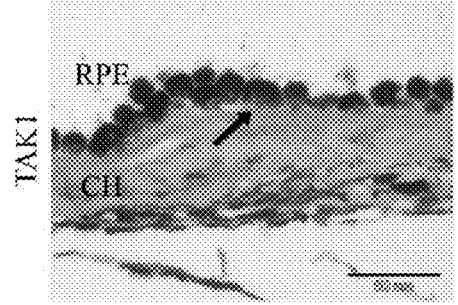
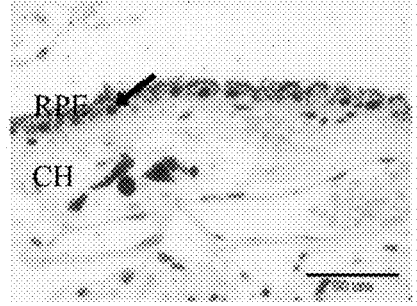
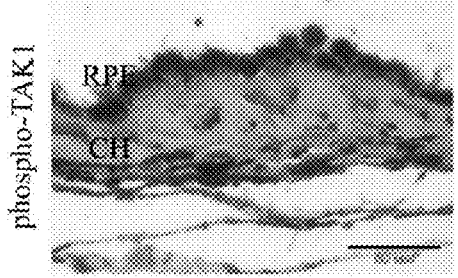
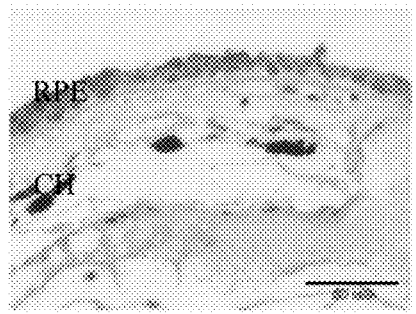
Figure 7C
Figure 7D

TREATMENTS FOR FIBROTIC DISEASES

CROSS REFERENCE TO RELATED APPLICATIONS

This is a Continuation-in-Part of International Patent Application No. PCT/IL2014/050882, filed Oct. 7, 2014, which claims the benefit of U.S. Provisional Patent Application No. 61/887,747, filed Oct. 7, 2013. Benefit is also claimed to U.S. Provisional Patent Application No. 62/139,761, filed Mar. 29, 2015. The foregoing patent applications are incorporated by reference in their entirety herein.

FIELD

Provided herein are methods for treatment for fibrotic ocular diseases and other fibrotic/fibrosis diseases that are associated with fibrosis, including proliferative vitreoretinopathy (PVR) and liver cirrhosis, by inhibiting the activity of transforming growth factor β activated kinase 1 (TAK1). Pharmaceutical compositions for use in the described treatments are also provided.

BACKGROUND

Fibrosis is the formation of excess fibrous connective tissue in an organ or tissue in a reparative or reactive process. Common and unique mechanisms regulate fibrosis in various fibroproliferative diseases. This can be a reactive and benign, such as in wound healing, or result in a pathological state leading to further complications. In response to injury, fibrosis is called scarring and if fibrosis arises from a single cell line it is called a fibroma. Physiologically the process of fibrosis involves deposit of connective tissue, which can obliterate the architecture and function of the underlying organ or tissue. Fibrosis can be used to describe the pathological state of excess deposition of fibrous tissue, as well as the process of connective tissue deposition in healing.

Proliferative vitreoretinopathy (PVR) is one example of an excessive fibrotic condition which occurs in the eye. PVR is a scarring process that develops as a complication associated with primary retinal detachment (RD) and perforating ocular trauma and it is the most common cause of surgical failure upon RD treatment (Ho et al., *Br J Ophthalmol* 1985, 69:584-587). PVR is a dynamic process characterized by the formation of fibrotic tissue on the retina, leading to complicated retinal detachment, preventing the reattachment of the detached retina and finally may cause blindness (Lambert et al., *Seminars in ophthalmology* 1995, 10:49-52). Retinal pigment epithelial (RPE) cells, which compose the external cell layer of the retina, are the most critical contributors to the development of the fibrotic response of PVR. During PVR, RPE cells undergo transformation into fibroblast-like cells through a process known as the epithelial-mesenchymal transition (EMT) (Takahashi et al., *J Biol Chem* 2010, 285:4060-4073). In the process of converting from epithelial into mesenchymal cells, they lose their epithelial characteristics such as polarity and specialized cell-to-cell contact, and acquire migratory mesenchymal properties (Grisanti et al., *Invest Ophthalmol Vis Sci* 1995, 36:391-405). These processes are mediated by the expression of cell surface molecules, cytoskeletal reorganization, and extracellular matrix (ECM) components (Thiery et al., *Cell* 2009, 139:871-890; Kalluri et al., *J Clin Invest* 2009, 119:1420-1428). EMT can be triggered by different signaling molecules such as epidermal growth factor (EGF) and fibroblast growth factor (FGF), however transforming growth factor beta-1 (TGF-β1) is considered the main regulator of EMT (Garweg et al., *Surv Ophthalmol* 2013, 58:321-329; Lamouille et al., I 2007, 178:437-451; Charteris, *Br J Ophthalmol* 1995, 79:953-960).

Similar to PVR, liver fibrosis is not an independent disease but rather a histological change caused by liver damage and inflammation. Liver damage causes hepatic stellate cells (HSC) to be over active and triggers increased ECM synthesis. As a result, greater than normal amounts of collagen fiber deposits accumulate in the extra-cellular spaces of the liver cells. The collagen deposits result in loss of blood infusion and cellular hardening. Liver fibrosis is the net result of the imbalance between the collagen fiber synthesis and decomposition. When fiber synthesis is very active and decomposition is suppressed, fibrosis will progress. Conversely, fibrosis can be reversed if inflammation and collagen synthesis is controlled.

Cirrhosis always develops from fibrosis. Although fibrosis and cirrhosis are distinguishable conditions, they are closely related. At the fibrosis stage, the amount of collagen increases and the ratio of fibro-connective tissue versus liver cellular tissue increases, but the liver lobular structures remain intact, and there is no pseudo-lobule formation. Cirrhosis consists of two pathological features: fibro-connective tissue hypertrophy and pseudo-lobule formation. At the cirrhosis stage, the liver's fundamental structure is deformed, and the framework of the liver begins collapse, making reversal of condition more difficult.

TGF-β-mediated EMT, a component of fibrosis pathogenesis, has been observed in a variety of cell types, including in the eye at the lens epithelial cells, corneal epithelial cells and other. Outside of the eye, TGF-β-mediated EMT has been observed in cells as varied as epithelial cells of the colon, lung epithelial cells and in the HSC cell (Saika S, *Lab Invest* 2006, 86:106-115).

Hepatic fibrosis is also known to result from an imbalance in TGF-β production. TGF-β is a multifunctional cytokine with an array of biological effects such as cell growth, differentiation, immunomodulation a double-edged sword effect, oxidative stress and endoplasmic reticulum (ER) stress (Desmouliere et al., *J Cell Biol* 1993, 122:103-111; Yoon et al., *Oncogene* 2005, 24:1895-1903). Intracellular signaling downstream to the TGF-β receptor complexes is mediated by the Smads family, the canonical pathway (Zhang et al., *Cell Res* 2009, 19:128-139). Recent reports have demonstrated that transforming growth factor β activated kinase 1 (TAK1), a member of the mitogen-activating protein (MAP) kinase kinase kinase family, is involved in the TGF-β signaling in the non-canonical pathway (Mu Y et al., *Cell Tissue Res* 2011, 347:11-20; Yamaguchi et al., *Science* 1995, 270:2008-2011; Kajino et al., *J Biol Chem* 2007, 282:9475-9481). But to date, the roles of TAK1 in RPE cell signaling and mediating PVR development were unknown. TAK1 is a serine/threonine kinase that is rapidly activated by TGF-β1 and subsequently activates other MAP kinases such as p38 (Ma et al., *Am J Physiol Renal Physiol* 2011, 300:F1410-1421; Wang et al., *J Biol Chem* 1997, 272:22771-22775). Moreover, studies indicate that TAK1 can regulate TGF-β-induced activation of Smad signaling by inducing Smad7 expression and also interfering with R-Smad transactivation by direct interaction with the MH2 domain of Smad proteins (Brown et al., *J Cell Biochem* 2007, 101:9-33). In addition to the role of TAK1 in the regulation of Smad function, there is cross-talk between the Smad and downstream targets of TAK1 such as p38 MAPK and ATF2 in the regulation of certain TGF-β1 target gene expression (Zhang et al., *Cell Res* 2009, 19:128-139; Mu Y et al., *Cell Tissue Res* 2011, 347:11-20). Even though TAK1 activation is associated with TGF-β1 signaling, it is well known that its activation can also be caused by various stimuli including: environmental stress, pro-inflammatory cytokines such as tumor necrosis factor-alpha (TNF-α), interleukin (IL)-1 and lipopolysaccharides (LPS) (Conner et al., *Biochem J* 2006, 399:427-434). Activated TAK1 can transduce signals to several downstream signaling cascades, including the MKK4/7-JNK, MKK3/6-p38 MAPK, and Nuclear Factor-kappa B (NF-kB)-inducing kinase (NIK)-IkB kinase (IKK) (Hanada et al., *J Biol Chem* 2001, 276: 5753-5759).

Currently available surgical options for the treatment of RD are pneumatic retinopexy, scleral buckling and pars plana vitrectomy (PPV). Although PVR is primarily managed surgically and there is large improvement in the surgical techniques, the numbers of PVR patients has remained constant from 1988 to 2003. Possible explanation for this high rate of PVR can be explained by the inability to prevent some level of cell adhesion and the subsequent pathological changes in-spite of the surgical procedure of vitrectomy. Thus, there is a continuing need to develop therapies for PVR that will enable better treatment outcomes for RD and prevent PVR- (and other ocular fibrosis-) related blindness.

Available treatments for liver fibrosis depend upon the stage of the condition. At an early stage of collagen fiber formation, fibers can be decomposed with water or weak acid, and are known as soluble fibers. At a more advanced stage, older fibers become thick and hard, and cannot be decomposed by water or weak acids. Such fibers require collagen enzymes for their decomposition. Anti-fibrosis herbal treatments are also in use. The goal of such treatments is to suppress the HSC, enhance the activities of collagen enzymes, and promote the decomposition of the fibers, reducing ECM. However, a continuing need exists for anti-fibrosis treatments that directly target the causal mechanisms of disease pathogenesis.

SUMMARY

Disclosed herein is the observation that TAK1 mediates TGF-β1-induced EMT in fibrotic cells, including RPE, hepatic cells, and colon tissue. This discovery enables the development of pharmaceutical compositions for treatment of fibrosis, ocular pathologies such as proliferative vitreoretinopathy (PVR), age-related macular degeneration (AMD), diabetic retinopathy, and other systemic diseases such as liver fibrosis, colitis, and lung fibrosis.

Accordingly, provided herein is a pharmaceutical composition for prevention or treatment of fibrosis, including liver fibrosis, and ocular diseases that are associated with fibrosis, such as PVR in a subject. The provided composition includes an inhibitor of at least one of the activation or kinase activity of transforming growth factor β activated kinase 1 (TAK1). Similarly-formulated compositions are also described for inhibiting or preventing EMT, such as in hepatic or in RPE cells in the retina Also described herein are methods for prevention or treatment of fibrosis, including ocular fibrotic conditions such as PVR and extra-ocular fibrotic conditions such as liver fibrosis, which include administering to a subject in need thereof, a therapeutically effective amount of an inhibitor of at least one of the activation or kinase activity of transforming growth factor β activated kinase 1 (TAK1), thereby preventing or treating the fibrosis.

Additionally described are methods for inhibiting epithelial-mesenchymal transition (EMT) in hepatic or retinal pigment epithelial cells in a subject, which include administering to a subject in need thereof, a therapeutically effective amount of an inhibitor of at least one of the activation or kinase activity of transforming growth factor β activated kinase 1 (TAK-1), thereby preventing or treating the liver fibrosis, colitis, pulmonary lung fibrosis, or PVR.

The foregoing and other objects, features, and advantages will become more apparent The foregoing and other objects, features, and advantages will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A: RPE cells were treated with TGF-β1 (2.5 ng/ml) for the indicated times or left untreated. The cells were then immunostained with phospho-Thr 187 TAK1 antibodies (green) and DAPI (blue) as described herein. Representative photographs of three independent experiments are shown. Scale bar is 10 μm for all images. B: The histogram demonstrating pixel intensity, measured using Image-J software, is based on three independent experiments. (Number of cells: Control 0=24, Control 4 hours=28, control 24 hours=21, control 48 hours=25; TGF-β1 4 hours=26, TGF-β24 hours=21, TGF-β48 hours=22). Statistics were computed using student t-test (Two tailed distribution equal variance). Data is expressed as the Mean±SD.

FIG. 2A: RPE cells were serum-starved for 16 hours, pretreated with 5Z-7-oxozeaenol (1 μM) or left untreated for 1 hour. The cells were then treated with TGF-β1 (2.5 ng/ml) as described herein for 24 h and immunostained with α-SMA antibodies (red) and DAPI (blue). Representative photographs of three independent experiments. The histogram in the bottom panel represents quantification of α-SMA antibody pixel intensity. FIG. 2B: RPE cells were serum-starved for 16 hours, then treated with mitomycin C (10 ng/ml) for 3 h. Thereafter, pretreated with 5Z-7-oxozeaenol (1 μM) or Dimethyl sulfoxide (DMSO) for 1 hour. Following this process a scratch was performed in the cell monolayer and the serum free medium was supplemented with TGF-β1 (2.5 ng/ml) or left unsupplemented. Scratches were photo-documented at the indicated times (top panel) and their width was measured using Image-J software. The histogram (bottom panel) demonstrates the percentage of remaining gap at each time point, relative to initial gap width, based on three independent experiments. Bars are Mean±SD. FIG. 2C: RPE cells were serum-starved for 16 hours then pretreated with 5Z-7-oxozeaenol (1 μM) or SB431542 (10 μM), or DMSO for 1 hour. Finally, the medium was replaced with serum free medium with or without TGF-β1 (2.5 ng/ml) and supernatants from the different treatments were collected after 24 hours. Total MMP-9 activities were processed by gelatin zymography (top panel) and the band intensity values were calculated by Quantity One® 1-D analysis software. Histogram demonstrating secretion levels of MMP-9 in the different treatments (bottom panel). Statistics were computed using student t-test (Two tailed distribution equal variance). Data is expressed as the Mean±SD.

FIG. 3A: RPE cells were plated on fibronectin-coated glass coverslips, serum-starved for 16 hours, pretreated with 5Z-7-oxozeaenol (1 μM) or SB431542 (10 μM), or DMSO for 1 hour, then treated with or without TGF-β1 for 2 days. Following treatment, the cells were stained with rhodamine-phalloidin (actin fibers-red) and DAPI (blue) and visualized by confocal microscopy. Scale bars: 20 μM. FIG. 3B: Serum-starved RPE cells pretreated with 5Z-7-oxozeaenol (1 μM) or DMSO for 1 hour, and were exposed to TGF-β as in FIG. 3A. Total RNA was extracted at each time point and qPCR was performed. Transcription levels of CTGF were determined after 6 h, 16 h and 24 h. Bars represent the specific mRNA amount relative to GAPDH mRNA in the same samples. All experiments were performed in triplicates. A representative histogram from two independent experiments is shown. FIG. 3C: RPE cells were plated and treated as in FIG. 3A. Following treatment, the cells were immunostained with E-cadherin antibodies (green) and DAPI (blue). Representative photographs of two independent experiments are shown.

FIG. 4A: Serum-starved RPE cells were pretreated with or without with 5Z-7-oxozeaenol (1 μM) for 1 hour and then with TGF-β (2.5 ng/ml) for the indicated times. Total protein extracts were analyzed by western blot using the indicated antibodies. The blot shows a representative result of four independent experiments. FIG. 4B: Levels of phospho-Smad2/3 were quantified and normalized to total Smad2/3 FIG. 4C: Statistical analysis of p-p38 and p-Smad3 activation normalized to p38 and Smad3 respectively, with or without TGF-β stimulation. The histograms present results of 5 independent experiments. Statistics were computed using student t-test (Two tailed distribution equal variance). Data is expressed as the Mean±SD.

FIG. 5A: RPE cells were pre-treated with or without 5Z-7-oxozeaenol (1 μM) and seeded in collagen lattices in full medium. The experiments were performed in triplicates. Lattices were photo-documented after 24 hours and measured using Image-J software. FIG. 5B: The histogram demonstrates the percentage of lattice area relative to initial gel area, based on three independent experiments. Bars are Mean±SD.

FIGS. 6A-6D: aberrant Activity of TAK1 in Human Pathologic Retina. FIGS. 6A and 6B: Retinal specimens, were immunostained with anti-TAK1 antibodies and hematoxylin (TAK1 expression is manifested by brown staining and black arrows), blue-hematoxylin. FIGS. 6C and 6D: Retinal specimens were treated as in A and stained with phospho-Thr 187 TAK antibodies (brown) and hematoxylin (blue), demonstrating aberrant activity of TAK1 in the retina of blind painful eyes. IR-inner retinal layers; INL-inner nuclear layer; OPL-outer plexiform layer; ONL-outer nuclear layer; S-photoreceptor segment (Scale bar=50 μm).

FIGS. 7A-7D: attenuated TAK1 Activity in RPE Cells with Pathology. FIGS. 7A and 7B: RPE cells of a retinal specimen were immunostained with TAK1 antibodies and hematoxylin. (TAK1 is manifested by brown staining and black arrows), blue-hematoxylin (N=5). FIGS. 7C and 7D: Retinal specimens treated as in A and stained with phospho-Thr 187 TAK antibodies (brown) and hematoxylin (blue), demonstrating aberrant activity of TAK1 in the RPE cells of blind painful eyes (Scale bar=50 μm).

FIG. 8A: Cell migration of RPE cells in in vitro scratch wound healing assay. RPE cells were treated with Mitomycin C for 3 hours. After the cells were treated with 1 μM 5Z-7 for 1 hour before adding 20 ng/ml TNFα and wounding on day 0. Photographs were taken at day 1 and 2, respectively, after the wound was made. FIG. 8B: Percentage of the gap size (*, P<0.05, t test); (**, P<0.01, t test).

DETAILED DESCRIPTION

Figure 1A:
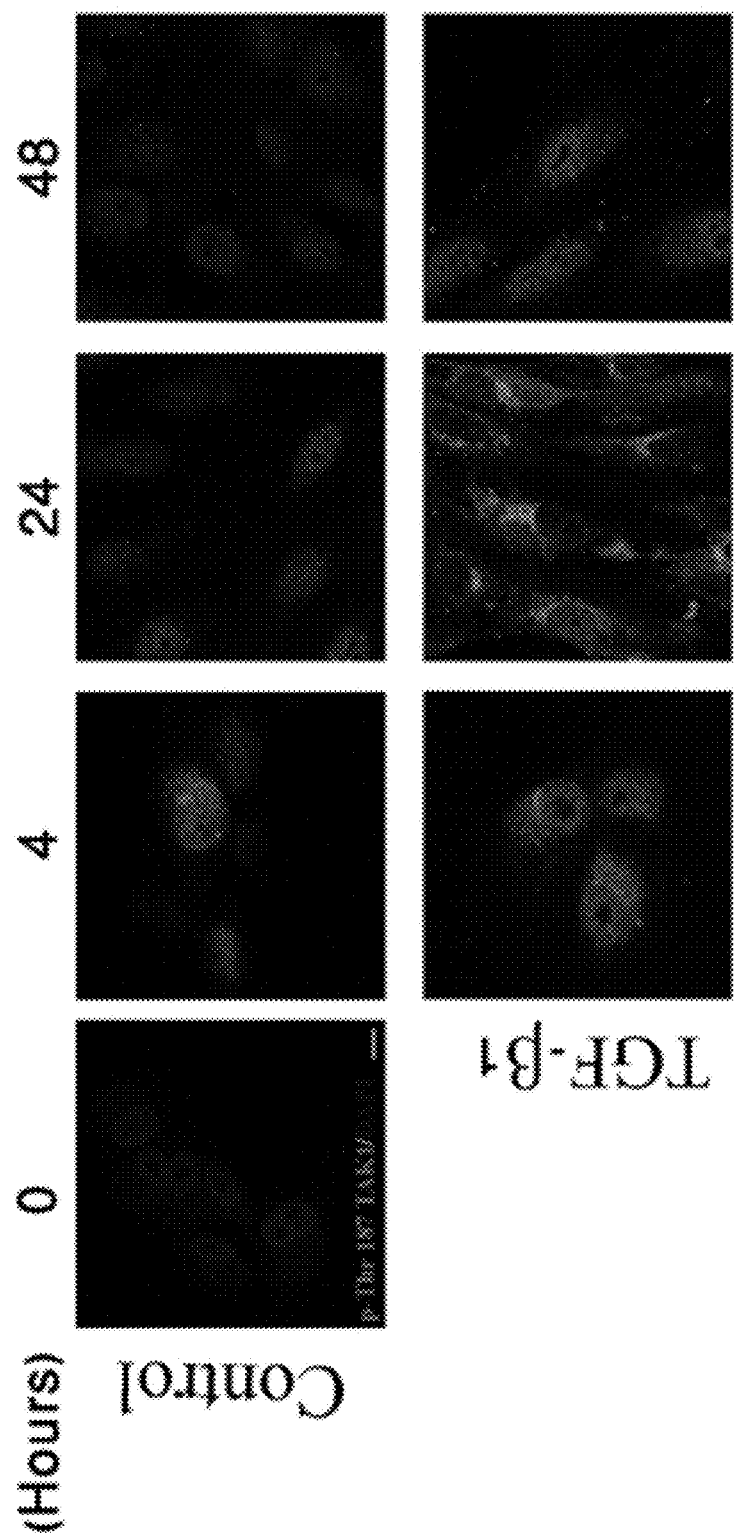
FIGS. 1A and 1B: TAK1 is activated upon TGF-β1 stimulation in RPE cells.

I. Abbreviations 5Z-7 5Z-7-oxozeaenol
EMT epithelial-mesenchymal transition
PVR proliferative vitreoretinopathy
RD retinal detachment
RPE retinal pigment epithelial
TAK1 transforming growth factor β activated kinase 1
TGF-β1 transforming growth factor beta-1
TNFα tumor necrosis factorα

II. Terms

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

In case of conflict, the present specification, including explanations of terms, will control. In addition, all the materials, methods, and examples are illustrative and not intended to be limiting.

Abnormal: Deviation from normal characteristics. Normal characteristics can be found in a control, a standard for a population, etc. For instance, where the abnormal condition is a disease condition, such as PVR, a few appropriate sources of normal characteristics might include an individual who is not suffering from the disease (e.g., PVR), a condition associated with the disease (e.g. RD), or a population standard of individuals believed not to be suffering from the disease.

Likewise, abnormal may refer to a process that is associated with a disease, such as abnormal EMT in RPE cells. The term "associated with" includes an increased risk of developing the disease as well as the disease itself. For instance, a certain abnormality (such as an abnormality in TAK1 activation) can be described as being associated with the biological conditions of abnormal EMT and the development of PVR.

Administration: The introduction of a composition into a subject by a chosen route. Administration of an active compound or composition can be by any route known to one of skill in the art to be useful for a particular target area. Administration can be local or systemic. In examples of treating fibrosis, including PVR, administration includes those routes by which an active compound can reach the intra-ocular space. Particular non-limiting examples include intra-ocular injection, topical drops, and intra-ocular implants.

Analog, derivative or mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in Remington (*The Science and Practice of Pharmacology*, 19th Edition (1995), chapter 28). A derivative is a biologically active molecule derived from the base structure. As used herein, "functional derivative" indicates that the derivative molecule retains the biological activity of the original molecule from which it derives. For example, a functional derivative of 5Z-7 will also inhibit TAK1. A mimetic is a molecule that mimics the activity of another molecule, such as a biologically active molecule. Biologically active molecules can include chemical structures that mimic the biological activities of a compound. It is acknowledged that these terms may overlap in some circumstances.

Animal: Living multi-cellular vertebrate organisms, a category that includes for example, mammals and birds. The term mammal includes both human and non-human mammals. Similarly, the term subject includes both human and veterinary subjects, for example, humans, non-human primates, dogs, cats, horses, and cows. The term "primate" includes both human and non-human primates. "Non-human primates" are simian primates such as monkeys, chimpanzees, orangutans, baboons, and macaques. Similarly, the term "subject" includes both human and veterinary subjects, such as non-human primates.

Antagonist: A molecule or compound that tends to nullify the action of another, or in some instances that blocks the ability of a given chemical to bind to its receptor or other interacting molecule, preventing a biological response. Antagonists are not limited to a specific type of compound, and may include in various embodiments peptides, antibodies and fragments thereof, and other organic or inorganic compounds (for example, peptidomimetics and small molecules).

Antibody: A polypeptide ligand comprising at least a light chain or heavy chain immunoglobulin variable region, which specifically recognizes and binds an epitope of an antigen. Antibodies are composed of a heavy and a light chain, each of which has a variable region, termed the variable heavy (VH) region and the variable light (VL) region. Together, the VH region and the VL region are responsible for binding the antigen recognized by the antibody. This includes intact immunoglobulins and the variants and portions of them well known in the art, such as Fab' fragments, F(ab)'$_2$ fragments, single chain Fv proteins ("scFv"), and disulfide stabilized Fv proteins ("dsFv"). The term also includes recombinant forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, Immunology, 3rd Ed., W.H. Freeman & Co., New York, 1997.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. These fused cells and their progeny are termed "hybridomas." Monoclonal antibodies include humanized monoclonal antibodies.

Antibodies for use in the methods, compositions, and systems of this disclosure can be monoclonal or polyclonal. Merely by way of example, monoclonal antibodies can be prepared from murine hybridomas according to the classical method of Kohler and Milstein (Nature 256:495-497, 1975) or derivative methods thereof. Detailed procedures for monoclonal antibody production are described in Harlow and Lane (*Antibodies, A Laboratory Manual*, CSHL, New York, 1988).

The terms bind specifically and specific binding refer to the ability of a specific binding agent (such as, an antibody) to bind to a target molecular species in preference to binding to other molecular species with which the specific binding agent and target molecular species are admixed. A specific binding agent is said specifically to recognize a target molecular species when it can bind specifically to that target. A neutralizing antibody or an inhibitory antibody is an antibody that inhibits at least one activity of a target—usually a polypeptide—such as by blocking the binding of the polypeptide to a ligand to which it normally binds, or by disrupting or otherwise interfering with a protein-protein interaction of the polypeptide with a second polypeptide.

Antisense inhibitor: Refers to an oligomeric compound that is at least partially complementary to the region of a target nucleic acid molecule to which it hybridizes. As used herein, an antisense inhibitor (also referred to as an "antisense compound") that is "specific for" a target nucleic acid molecule is one which specifically hybridizes with and modulates expression of the target nucleic acid molecule. As used herein, a "target" nucleic acid is a nucleic acid molecule to which an antisense compound is designed to specifically hybridize and modulation expression. Nonlimiting examples of antisense compounds include primers, probes, antisense oligonucleotides, siRNAs, miRNAs, shRNAs and ribozymes. As such, these compounds can be introduced as single-stranded, double-stranded, circular, branched or hairpin compounds and can contain structural elements such as internal or terminal bulges or loops. Double-stranded antisense compounds can be two strands hybridized to form double-stranded compounds or a single strand with sufficient self complementarity to allow for hybridization and formation of a fully or partially double-stranded compound.

Effective amount of a compound: A quantity of compound sufficient to achieve a desired effect in a subject being treated. An effective amount of a compound can be administered in a single dose, or in several doses, for example daily, during a course of treatment. However, the effective amount of the compound will be dependent on the compound applied, the subject being treated, the severity and type of the affliction, and the manner of administration of the compound.

Fibrosis: A cellular reaction to injury and inflammation; the abnormal increase in connective tissue. Fibrosis can develop in a wide range of cell types, including retinal and hepatic cells. In particular examples, fibrotic conditions are a precursor to more significant conditions including the inability to repair detached retina and liver cirrhosis. In particular embodiments the treatments for fibrosis include treatment of ocular fibrotic diseases (disease associated with fibrosis), and diseases including but not limited to liver cirrhosis, Arthrofibrosis, Retroperitoneal fibrosis, Nephrogenic systemic fibrosis, colitis, Crohn's Disease, Keloid, Idiopathic pulmonary fibrosis (IPF), cystic fibrosis (CF), Small bowel fibrosis, and Proliferative vitreoretinopathy (PVR) Ocular disorder resultant from fibrosis, Age-related macular degeneration, Diabetic retinopathy in particular proliferative, Retinopathy of prematurity, Retinal disease associated with neovascularization, Corneal scaring, Glaucoma Surgery Scarring and others.

Inhibiting protein activity: To decrease, limit, or block an action, function or expression of a protein. The phrase inhibit protein activity is not intended to be an absolute term. Instead, the phrase is intended to convey a wide-range of inhibitory effects that various agents may have on the normal (for example, uninhibited or control) protein activity. Inhibition of protein activity may, but need not, result in an increase in the level or activity of an indicator of the protein's activity. By way of example, this can happen when the protein of interest is acting as an inhibitor or suppressor of a downstream indicator. Thus, protein activity may be inhibited when the level or activity of any direct or indirect indicator of the protein's activity is changed (for example, increased or decreased) by at least 10%, at least 20%, at least 30%, at least 50%, at least 80%, at least 100% or at least 250% or more as compared to control measurements of the same indicator. Inhibition of protein activity may also be effected, for example, by inhibiting expression of the gene encoding the protein or by decreasing the half-life of the mRNA encoding the protein.

Modulator: An agent that increases or decreases (modulates) the activity of a protein or other bio-active compound, as measured by the change in an experimental biological parameter. A modulator can be essentially any compound or mixture (for example, two or more proteins), such as a polypeptide, a small molecule, a hormone, a nucleic acid, a sugar, a lipid and the like.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of the compounds herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or composition capable of inducing a desired therapeutic or prophylactic effect when properly administered to a subject or a cell. Incubating includes exposing a target to an agent for a sufficient period of time for the agent to interact with a cell. Contacting includes incubating an agent in solid or in liquid form with a cell.

Preventing or treating a disease: Preventing a disease refers to inhibiting the full development of a disease, for example inhibiting the development of PVR in a person who has a detached retina or inhibiting the progression of EMT in RPE cells exposed to blood-borne cytokines, or the inhibition of liver fibrosis in inflamed liver tissue. Treatment refers to a therapeutic intervention that ameliorates a sign or symptom of a disease or pathological condition after it has begun to develop. In particular examples, treatment of a disease can include inhibition of disease progression. For example, treatment of PVR can result from inhibition of EMT in RPE cells, or treatment of inflamed liver tissue can inhibit hepatic fibrosis and cirrhosis.

Small molecule inhibitor: A molecule, typically with a molecular weight less than 1000, or in some embodiments, less than about 500 Daltons, wherein the molecule is capable of inhibiting, to some measurable extent, an activity of some target molecule, such as an activator of TAK1.

Transforming growth factor-beta activated kinase 1 (TAK1): TAK1 is a member of the MAPKKK family, and was first reported as a regulator of MAP kinase signaling induced by TGF-β or oxidative stress. TAK1 is known to be activated by stress signals as well as proinflammatory cytokines, and is involved in activation of p38 and JNK signaling. TAK1 was originally known as MAP3K7.

III. Overview of Several Embodiments

Provided herein is a pharmaceutical composition for prevention or treatment of fibrosis, including colitis, liver fibrosis and PVR in a subject, which includes an inhibitor of at least one of the activation or kinase activity of transforming growth factor β activated kinase 1 (TAK1).

In particular embodiments, the pharmaceutical composition includes a TAK1 inhibitor that inhibits the activation of TAK1. In other embodiments, the TAK1 inhibitor inhibits the kinase activity of active TAK1.

In particular embodiments, the TAK1 inhibitor is a peptide, antibody, small molecule, or anti-sense nucleic acid.

In further embodiments, the pharmaceutical composition includes an activator of a protein phosphatase selected from the group consisting of protein phosphatase 1A (PPM1A), protein phosphatase 1B (PPM1B), protein phosphatase 6 (PP6), and dual specificityprotein phosphatase 14 (DUS14).

In still further embodiments, the pharmaceutical composition includes an antibody that specifically binds to, and blockades, the kinase activation site on TAK1.

Methods of using the provided pharmaceutical compositions for prevention or treatment of fibrosis, including liver fibrosis. Colitis, and proliferative vitreoretinopathy (PVR) in a subject are also disclosed herein, which include administering a therapeutically effective amount of at least one of the described pharmaceutical compositions to a subject in need thereof, thereby preventing or treating the fibrosis, including liver fibrosis and PVR.

In particular embodiments involving treatment of PVR, the inhibitor is administered to the subject after retinal detachment. In other embodiments, the inhibitor is administered to the subject prior to, during, or after surgery for treatment of retinal detachment.

The pharmaceutical compositions for prevention or treatment of fibrosis, including liver fibrosis and PVR can also be used for preventing or inhibiting epithelial-mesenchymal transition (EMT) in multiple cell types, including in retinal pigment epithelial cells and hepatic cells, and in methods for preventing or inhibiting epithelial-mesenchymal transition (EMT) in retinal pigment epithelial cells.

IV. TAK1 Inhibition for Treatment of Fibrosis

EMT in RPE is the pathway by which PVR develops following retinal detachment. Prior to this disclosure, although TGF-β1 was associated with EMT in a variety of cell types, no direct association with EMT in retina had ever been determined. Moreover, the expression of TAK1 in retina, and the role of TGF-β1-activated TAK1 in retinal EMT, and by extension development of PVR was unknown.

Provided herein is the discovery that TAK1 is an essential mediating factor for TGF-β1-induced PVR following retinal detachment. Similarly, also shown is the observation that TAK1 provides a similar function in hepatic EMT. These discoveries enable the development of pharmaceutical agents that can be used to inhibit fibrosis in general, and particularly retinal EMT and development of PVR following retinal detachment.

The pharmaceutical compositions described herein include any agent that can inhibit the activation of TAK1, or can prevent the ability for activated TAK1 to phosphorylate its target molecules. Non-limiting examples of TAK1 inhibitory agents include small molecule inhibitors, peptides, antibodies, and antisense nucleic acids.

In particular embodiments, the agents for use in the described compositions and methods can inhibit the activation (e.g. phosphorylation) of TAK1, for example at the TAK1 Thr-187 residue. In particular embodiments, the agent is a blocking or neutralizing antibody that specifically recognizes TAK1 and prevents the phosphorylation of Thr-187.

In other embodiments, the agents for use in the described compositions and methods are zearalenones having hydroxyl groups at both of the 8- and 9-positions, for example 5Z-7 oxozeanol (also known in the art as FR148083, L-783,279, and LL-Z 1640-2), and derivatives thereof. Description of TAK1-inhibitory zearalenone derivatives can be found at least in International Patent Publication No. WO2002/48135, the contents of which are incorporated by reference herein.

In particular embodiments, the TAK1 inhibitor is 5Z-7 oxozeaenol, having a structure set out in Formula I:

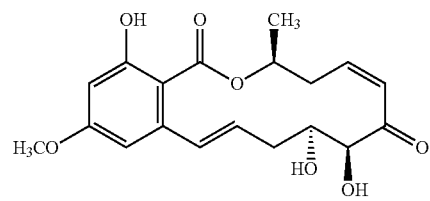 [SMILES: COc1cc(O)c2c(c1)/C=C/C[C@H](O)[C@H](O)C(=O)/C=C\C[C@H](C)OC2=O]

In other embodiments, the TAK1 inhibitor is 5Z-7 benzene 6-7, having a structure set out in Formula II:

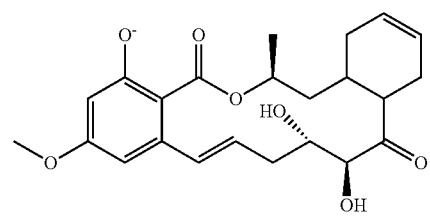 [SMILES: COc1cc([O-])c2c(c1)/C=C/C[C@H](O)[C@H](O)C(=O)C1CC=CCC1C[C@H](C)OC2=O]

In other embodiments, the TAK1 inhibitor is 5Z-7 pharmacophore Fluorine-14, having a structure set out in Formula III:

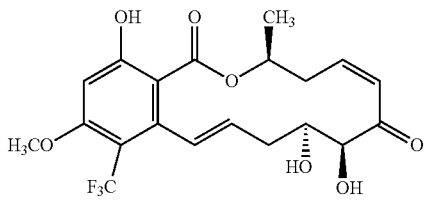 [SMILES: COc1cc(O)c2c(c1C(F)(F)F)/C=C/C[C@H](O)[C@H](O)C(=O)/C=C\C[C@H](C)OC2=O]

In still other embodiments, the TAK1 inhibitor is 5Z-7 pharmacophore Fluorine-1, having a structure set out in Formula IV:

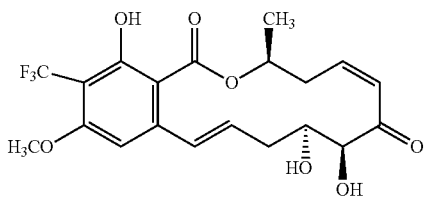 [SMILES: COc1cc2c(c(O)c1C(F)(F)F)C(=O)O[C@@H](C)C/C=C\C(=O)[C@@H](O)[C@@H](O)C/C=C/2]

In still other embodiments, the TAK1 inhibitor is 5Z-7-Fluorine 6-7, having a structure set out in Formula V:

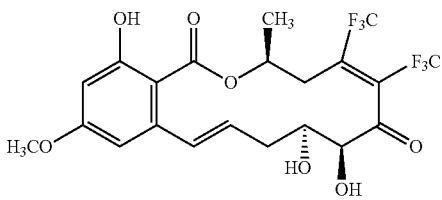 [SMILES: COc1cc(O)c2c(c1)/C=C/C[C@H](O)[C@H](O)C(=O)/C(C(F)(F)F)=C(/C(F)(F)F)C[C@H](C)OC2=O]

It will be appreciated that substitutions to the structures pictured herein as Formulas I-V, and which retain the overall structure of the formulas, are contemplated for use in described methods of fibrosis treatment.

Certain phosphatases, including but not limited to protein phosphatase 1A (PPM1A), protein phosphatase 1B (PPM1B), protein phosphatase 6 (PP6), and dual specificity-typrotein phosphatase 14 (DUS14) are associated with maintenance of TAK1 in a non-activated (e.g. naïve) state. In certain embodiments, increased activity of such phosphatases can inhibit activation of TAK1. In particular examples, the described composition includes the small molecule activator NPLC0393 or a derivative thereof, which can increase the activity of the PPM1A and/or PPM1B phosphatases (Wang et al., PLoS One 2010 Dec. 6; 5(12): e14230).

In other embodiments the TAK1 inhibitor is an agent which inhibits the kinase activity of activated TAK1. In particular embodiments, the agent is a neutralizing antibody that specifically recognizes activated TAK1 and blockades its activity. In other embodiment, the inhibitor is a small molecule mimetic agents of a blockading antibody.

The ability for any of the described agents to inhibit the activation and/or activity of TAK1 can be determined (if not known) by any method known in the art, including those described in the Examples section below.

V. Methods for Inhibition of EMT and Treatment of Fibrosis, Including Liver Fibrosis and PVR The described TAK1-inhibiting compositions can be used in methods of inhibition of EMT in varied cell types, including but not limited to RPE cells (for treatment or prevention of PVR), in hepatic cells (for treatment of liver fibrosis and prevention of cirrhosis), colon cells (for treatment of colitis), and in epithelial lung cells (for treatment of pulmonary lung fibrosis). EMT occurs in RPE cells following retinal trauma, such as retinal detachment. Accordingly, the methods of treatment described herein relate to administration of a TAK1 inhibiting agent to a subject who has experienced retinal trauma. Similarly, the methods of treatment described herein relate to a subject who has injury or inflammation in the liver.

Surgery is the most common treatment for retinal trauma, and it is the scarring resultant from PVR which is known to decrease successful outcomes of RD surgery. In particular embodiments, the TAK1 inhibitor (such as 5Z-7 oxozeanol, and functional derivatives thereof, such as a compound set out herein as Formulas I-IV) is administered to a subject following RD, but prior to RD surgery. In other embodiments, the TAK1 inhibitor is administered during surgery, or as a post-operative treatment. It will be appreciated that when administered post-operatively, the TAK1 inhibitor can be administered directly after RD surgery as well as throughout any recovery period following retinal trauma and RD surgery. In particular embodiments, the TAK1 inhibitor is administered within the first post-operative day, one, two, three, four, five, six days, or one, two, three, four, or more weeks after surgery.

Similarly, in a subject who has experienced a trauma to the liver (or other organ sensitive to fibrosis development following trauma), administration of a compound described herein can treat or prevent liver fibrosis and by extension, prevent the development of cirrhosis. Such treatment can be administered to the subject within, one, two, three, four, five, six days, or one, two, three, four, or more weeks after the liver trauma.

As described below, the administration of a TAK1 inhibitor can be by any route and in any form suitable for delivery of the inhibitor to an effected area, such as hepatic cells and RPE cells.

VI. Pharmaceutical Compositions and Modes of Administration

It is contemplated that the pharmaceutical agents for use in the described treatments can be supplied in any pharmaceutically acceptable compositions.

Among the pharmaceutical compositions specifically contemplated in the present disclosure are pharmaceutically acceptable acid or base addition salts of small molecule inhibitors of TAK1 (such as 5Z-7 oxozeanol, and derivatives thereof, including a compound set forth herein as Formula I-V). The phrase "pharmaceutically acceptable acid or base addition salts" includes therapeutically active non-toxic acid and non-toxic base addition salt forms which a TAK1 inhibitor is able to form. Such compounds which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Small molecule TAK1 inhibitors which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The terms acid or base addition salt also comprise the hydrates and the solvent addition forms of the small molecules in the described compositions. Examples of such forms are, for instance, hydrates, alcoholates and the like.

Also contemplated for use in methods and compositions described herein are sterochemcially isomeric forms of the described small molecule. The term stereochemically isomeric form includes all possible compounds made up of the same atoms bonded by the same sequence of bonds, but having different three-dimensional structures that are not interchangeable. Unless otherwise mentioned or indicated, the chemical designation of a compound encompasses the mixture of all possible stereochemically isomeric forms that the compound may possess. Such mixture may contain all diastereomers and/or enantiomers of the basic molecular structure of the compound. Also contemplated are all stereochemically isomeric forms in pure form or in admixture with each other.

Various intraocular delivery systems are known and can be used to administer the peptides, antibodies, and small molecules described herein. Such systems include, for example, encapsulation in liposomes, microparticles, microcapsules, recombinant cells capable of expressing therapeutic molecule(s) (see, e.g., Wu et al., *J. Biol. Chem.* 262, 4429, 1987), construction of a therapeutic nucleic acid (expressing the described peptide or antibody) as part of a retroviral or other vector, and the like. Methods of introduction include, but are not limited to, intraocular injection, topical administrations, and as delivered by use of an intraocular implant. It is also contemplated that the described TAK1 inhibitors may be administered together with other biologically active agents.

In a specific embodiment, it may be desirable to administer the described pharmaceutical treatments as an implant (e.g., implants formed from porous, non-porous, or gelatinous materials, including membranes, such as sialastic membranes or fibers), and the like. In another embodiment, therapeutic agents are delivered in a vesicle, in particular liposomes (see, e.g., Langer, *Science* 249, 1527, 1990; Treat et al., in *Liposomes in the Therapy of Infectious Disease and Cancer*, Lopez-Berestein and Fidler (eds.), Liss, N.Y., pp. 353-365, 1989).

In yet another embodiment, the TAK1 inhibitor can be delivered in a controlled release system. In one embodiment, polymeric materials can be used (see, e.g., Ranger et al., *Macromol. Sci. Rev. Macromol. Chem.* 23, 61, 1983; Levy et al., *Science* 228, 190, 1985; During et al., *Ann. Neurol.* 25, 351, 1989; Howard et al., *J. Neurosurg.* 71, 105, 1989). Other controlled release systems, such as those discussed in the review by Langer (*Science* 249, 1527 1990), can also be used.

The vehicle in which the TAK1 inhibitor is delivered can include pharmaceutically acceptable compositions of the compounds, using methods well known to those with skill in the art. For instance, in some embodiments, the agents described herein are typically contained in a pharmaceutically acceptable carrier. The term "pharmaceutically acceptable" means approved by a regulatory agency of the federal or a state government or listed in the U.S. Pharmacopoeia or other generally recognized pharmacopoeia for use in animals, and, more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable, or synthetic origin, such as peanut oil, soybean oil, mineral oil, sesame oil, and the like. The medium may also contain conventional pharmaceutical adjunct materials such as, for example, pharmaceutically acceptable salts to adjust the osmotic pressure, lipid carriers such as cyclodextrins, proteins such as serum albumin, hydrophilic agents such as methyl cellulose, detergents, buffers, preservatives and the like.

Examples of pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The therapeutic, if desired, can also contain minor amounts of wetting or emulsifying agents, or pH buffering agents. The therapeutics can take the form of solutions, suspensions, emulsion, tablets, pills, capsules, powders, sustained-release formulations, and the like. The therapeutic can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, and the like. A more complete explanation of parenteral pharmaceutical carriers can be found in Remington: *The Science and Practice of Pharmacy* (19th Edition, 1995) in chapter 95.

Embodiments of other pharmaceutical compositions are prepared with conventional pharmaceutically acceptable counter-ions, as would be known to those of skill in the art.

Therapeutic preparations will contain a therapeutically effective amount of at least one active ingredient, preferably in purified form, together with a suitable amount of carrier so as to provide proper administration to the patient. The formulation should suit the mode of administration.

The effective amount of a TAK1 inhibitor in the described pharmaceutical compositions can be determined by standard clinical techniques. The precise dose to be employed in the formulation will also depend on the route of administration, and should be decided according to the judgment of the health care practitioner and each patient's circumstances. Exemplary dosages of the individual compounds are described herein, but myriad other dosage regimens are encompassed by this disclosure. An example of an additional dosage range is 0.1 to 200 mg/kg body weight in single or divided doses. Another example of a dosage range is 1.0 to 100 mg/kg body weight in single or divided doses.

The specific dose level and frequency of dosage for any particular subject may be varied and will depend upon a variety of factors, including the activity of the specific compound, the metabolic stability and length of action of that compound, the age, body weight, general health, sex, diet, mode and time of administration, rate of excretion, drug combination, and severity of the condition of the host undergoing therapy.

The following examples are provided to illustrate certain particular features and/or embodiments. These examples should not be construed to limit the disclosure to the particular features or embodiments described.

EXAMPLES

Example 1: TGF-β1 Activates TAK1 MAP Kinase in RPE

TAK1 is a known mediator of TGF-β1 signaling, but has not been detected (in either inactive or active forms) in RPE cells. This example shows that TAK1 is expressed and is activated in RPE cells.

Figure 1B:
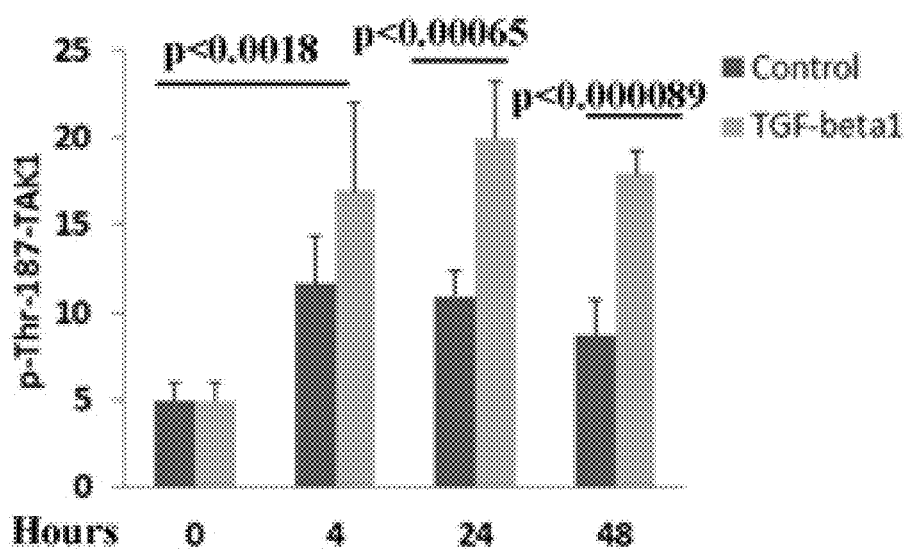

To investigate the kinetics and the expression pattern of activated TAK1 in RPE cells upon TGF-β1 treatment, RPE cells were immunostained using phospho-TAK1 antibodies, which specifically recognize the activated form of TAK1 phosphorylated on Thr 187. As shown in FIGS. 1A and 1B, TAK1 activation, observable in the non-nuclear staining, gradually increased in the treated cells, reaching a peak 24 hours post treatment and then declined. In contract, the control cells displayed only marginal levels of activated TAK1 with no significant changes, thus demonstrating the specific activation of TAK1 by TGF-β1 in the RPE cells.

Example 2: Inhibition of TAK1 Halts the EMT Process Upon TGF-β1 Stimulation in RPE Cells It is known that EMT can be mediated by a variety of factors. This example shows that TGF-β1-stimulated EMT occurring in RPE is mediated by activated TAK1.

Figure 2A:
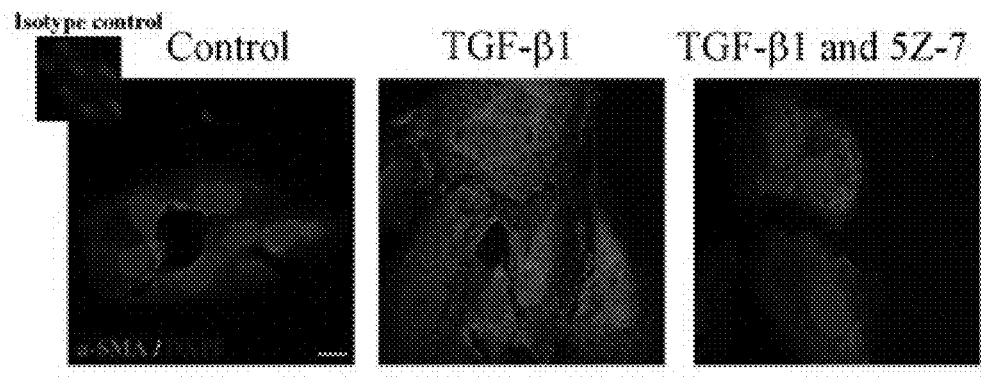
FIGS. 2A-2C TAK1 regulates RPE cells EMT phenotype upon TGF-β stimulation.
Figure 2A:
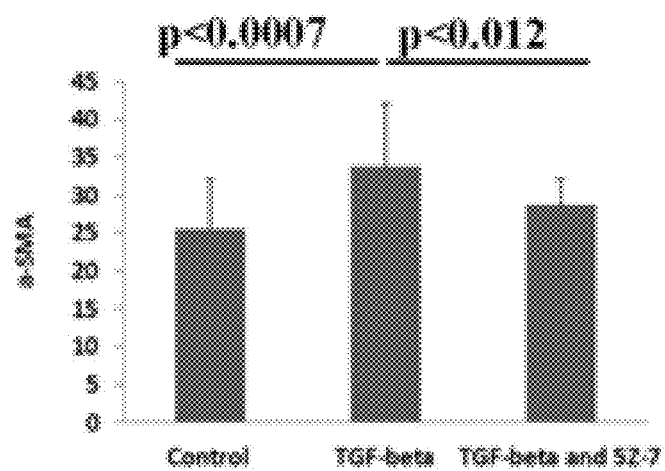

EMT of RPE cells is known to be mediated by TGF-β1 and characterized by increased expression of α-SMA, enhanced cell migration, and secretion of MMPs. To address a possible involvement of TAK1 in TGF-β1-induced RPE cell transdifferentiation, we studied the effects of specific TAK1 inhibitors on this process. A crucial step in transdifferentiation of RPE cells to myofibroblasts is the de novo synthesis of α-SMA (Hinz et al., *Am J Pathol* 2001, 159:1009-1020). To observe this process in vitro, we stimulated RPE cells with TGF-β1 for 2 days under serum-free conditions with or without the presence of a TAK1 inhibitor (5Z-7-oxozeaenol), or DMSO as a control (FIG. 2A). As can be seen in FIG. 2A, while TGF-β1 considerably stimulated α-SMA expression, the TAK1 inhibitor significantly attenuated this process.

Figure 2B:
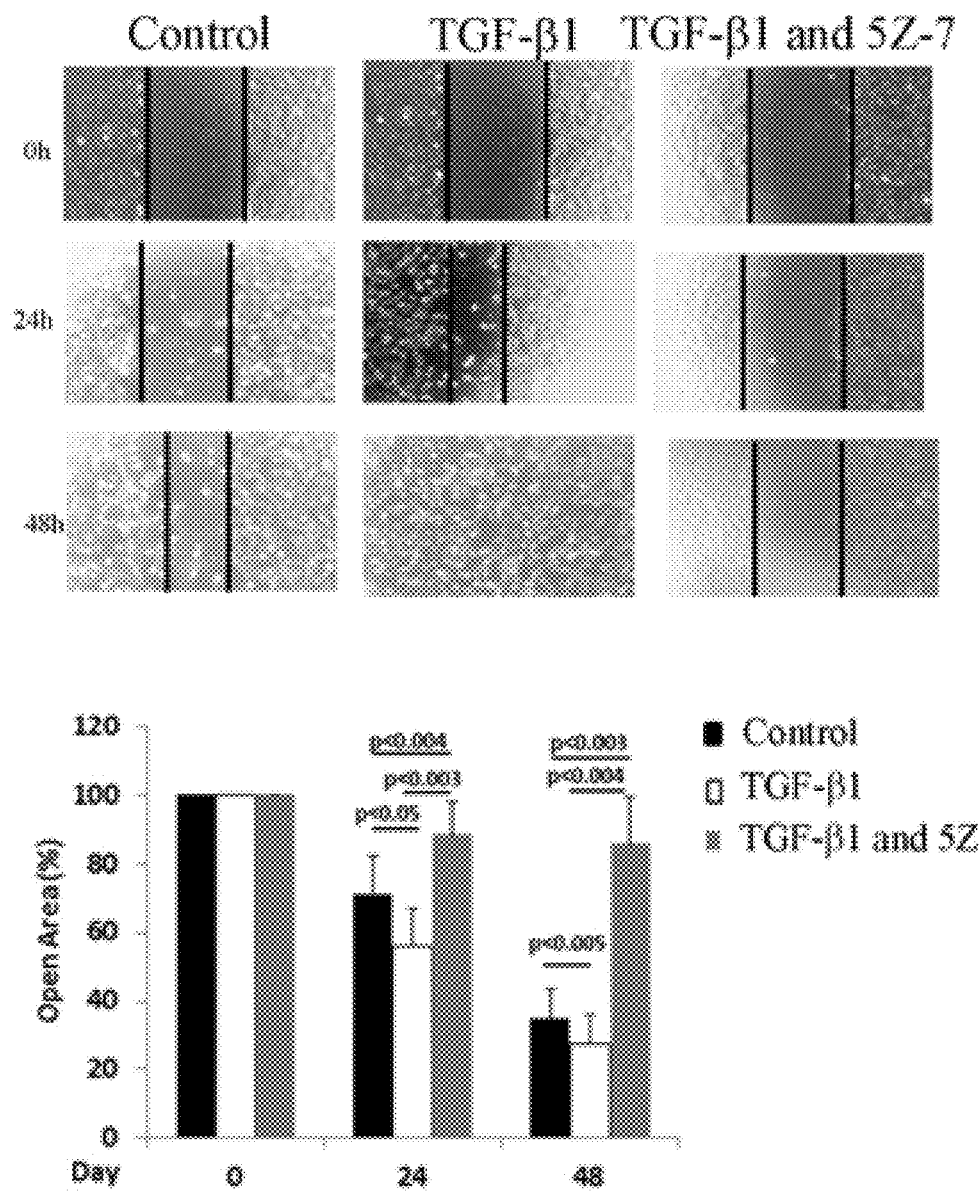
Figure 8A:
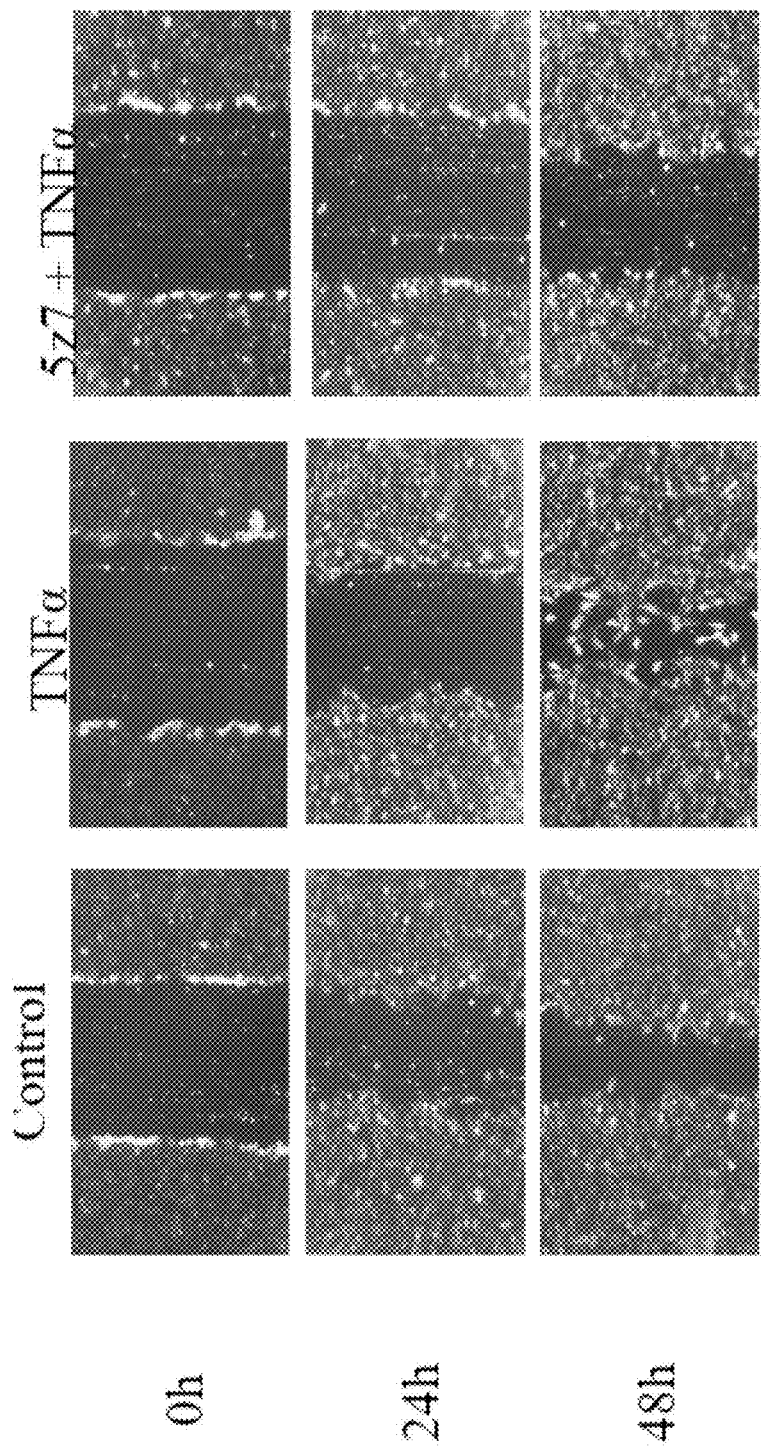
FIGS. 8A and 8B TAK1 regulates RPE cells EMT phenotype upon TNFα stimulation show that a TAK1 inhibitor reduced the migration rates of RPE cells treated with TNFα.
Figure 8B:
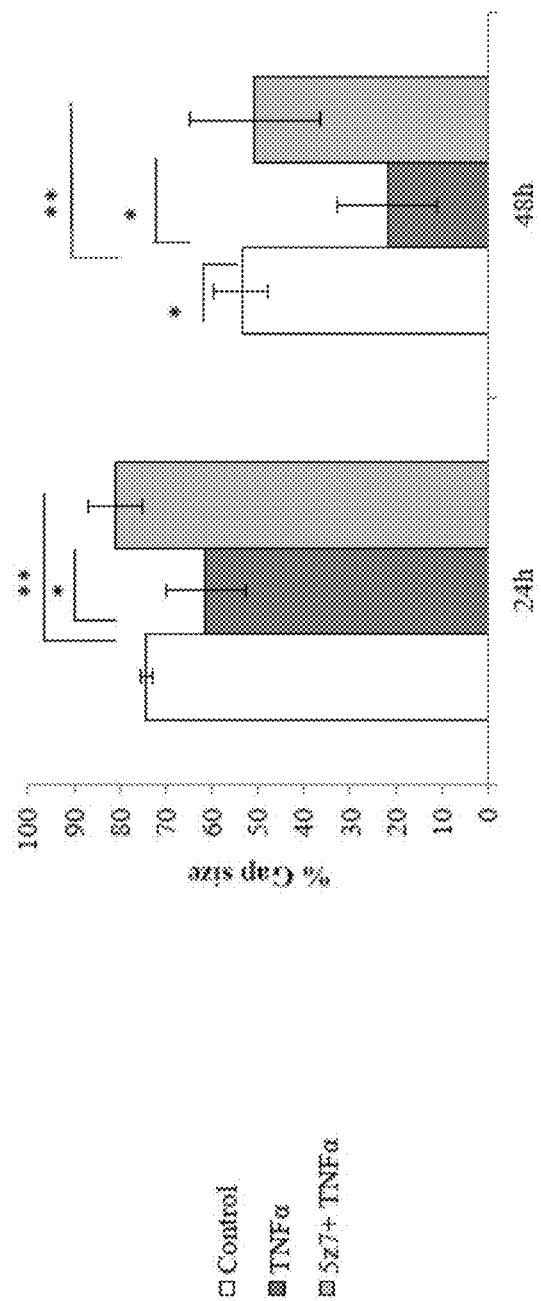

To further support the finding that TAK1 mediated EMT in RPE, we examined the migratory capacity of RPE cells, a well-known marker for EMT (Lee et al., *J Cell Biol* 2006, 172:973-981). Cell migration was tested by the scratch assay. The assay was performed on RPE cells pretreated or untreated with TAK1 inhibitor prior to stimulation with TGF-β1. As expected, addition of TGF-β1 significantly enhanced the migration of the RPE cells (FIG. 2B, TGF-β1) compared to control cells. At 24 hours, in the TGF-β1 treated culture, a major portion of the cells had already migrated into the wounded area, displaying almost complete wound closure at 48 hours. In contrast, the addition of 5Z-7-oxozeaenol to TGF-β1 stimulated cells abolished their migratory capacity. Similarly, as shown in FIGS. 8A and 8B, treatment with 5Z-7 inhibited the migration rates of RPE cells treated with TNFα.

Figure 2C:
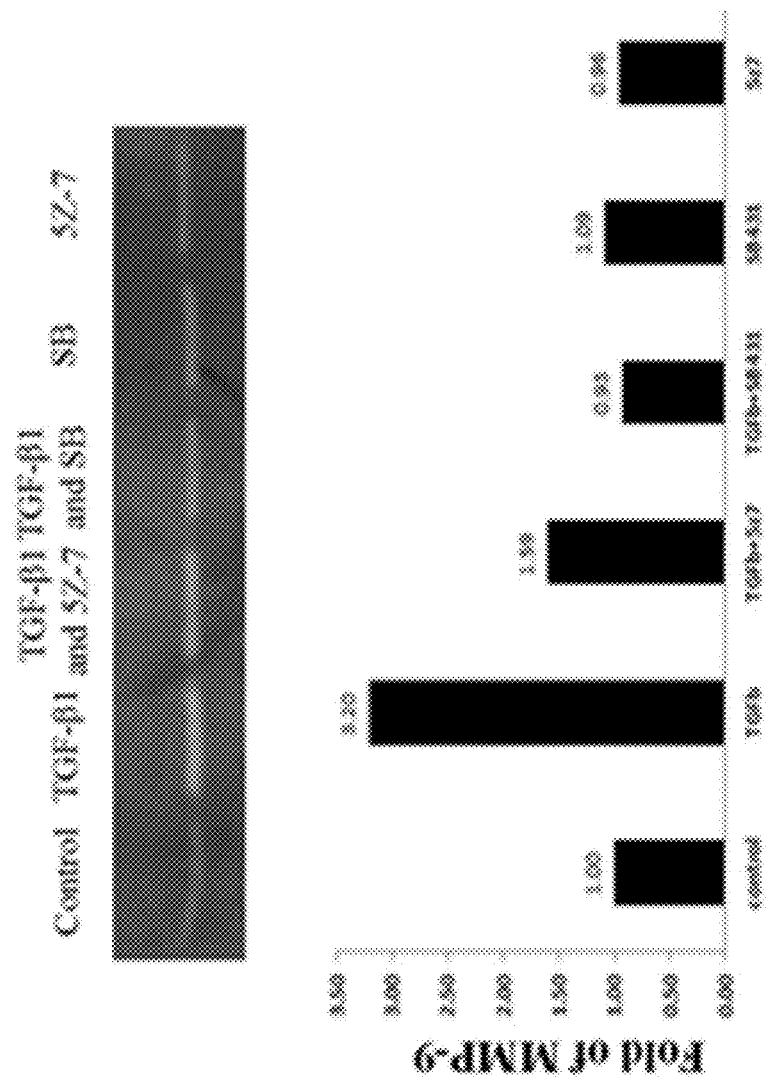

Emerging evidence indicates that matrix metalloproteinases (MMPs) can stimulate processes associated with EMT such as enhancement of cell invasion and migration (Lee et al., *Invest Ophthalmol Vis Sci* 2007, 48:4291-4299). Most reports suggest that predominance of MMP-2, -3 and -9 proteins correlate with worse prognosis. Examining the role of TAK1 in the activation of MMP-9 by gelatin zymography demonstrated that after 24 hours of exposure, TGF-β1 stimulated 92-kDa MMP-9 protein activity in RPE cells (FIG. 2C). The activity of MMP-9 was significantly higher (3.2 fold) than the control group. Treatment of the cells with TAK1 inhibitor prior to TGF-β1 stimulation resulted in decreased MMP-9 activity, only 1.59 fold higher than the control group. Moreover, pre-treatment with SB431542, a specific inhibitor of the TGF-β1 receptor, completely abolished the activation of MMP-9. Thus, this result demonstrates that TGF-β1 is an inducer of MMP-9 activation in RPE cells and this phenomenon is mediated by TAK1.

Figure 3A:
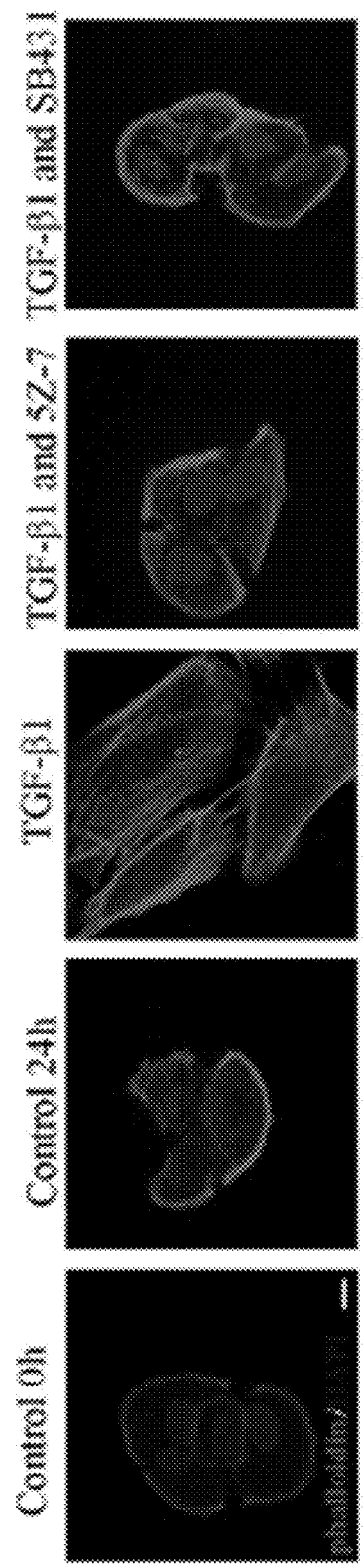
FIGS. 3A-3C show that TGF-β regulates morphological and transcriptional changes in RPE cells through TAK1.

In addition to the secretion of MMPs and increased migratory capacity, several morphological changes underlie EMT (Lamouille et al., I 2007, 178:437-451). One of the phenotypes characterizing EMT is an increase in cell size mediated by TGF-β1 (Lamouille et al., I 2007, 178:437-451; Casaroli-Marano et al., *Invest Ophthalmol Vis Sci* 1999, 40:2062-2072). Examination of RPE cells treated with TGF-β1 confirmed our expectations: cells were indeed enlarged 24 hour post treatment (FIG. 3A). In contrast, RPE cells that were treated with TAK1 inhibitor prior to TGF-β1 treatment demonstrated a minimal number of hypertrophic RPE cells. Concomitantly, we found that employing SB431542, a specific inhibitor of TGF-β1 receptor, abolished the increase in cell size, similarly to the results with TAK1 inhibitor (FIG. 3A).

Figure 3B:
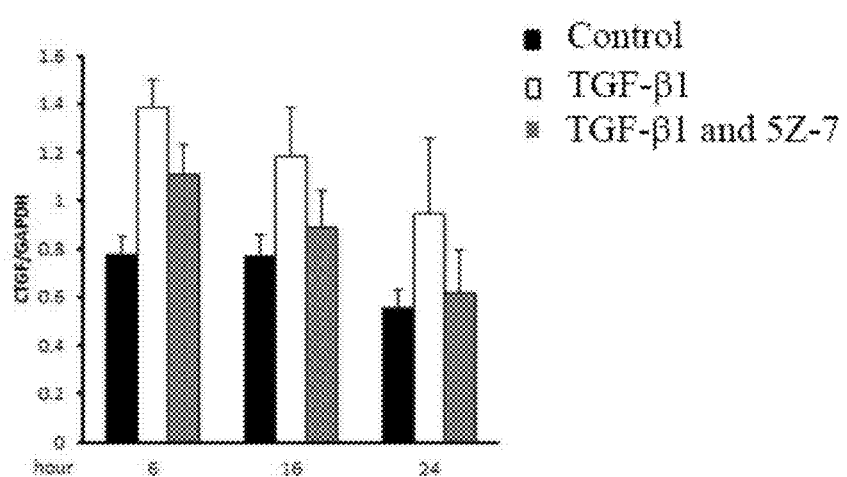

CTGF, an important stimulant of fibrosis, functions as a downstream mediator of TGF-β, stimulating cell proliferation and cell matrix deposition (He et al., *Invest Ophthalmol Vis Sci* 2008, 49:4078-4088). We examined the association between TGF-β1 and CTFG expression in RPE cells by Real Time PCR (FIG. 3B). Our results show that CTGF expression is significantly enhanced as early as 6 hours post TGF-β1 stimulation, and the effect lasts for at least 24 hours. Addition of the TAK1 inhibitor gradually reduced the levels of CTGF up to 24 hours post treatment, indicating that CTGF is a downstream mediator of TGF-β via TAK1 pathway.

Figure 3C:
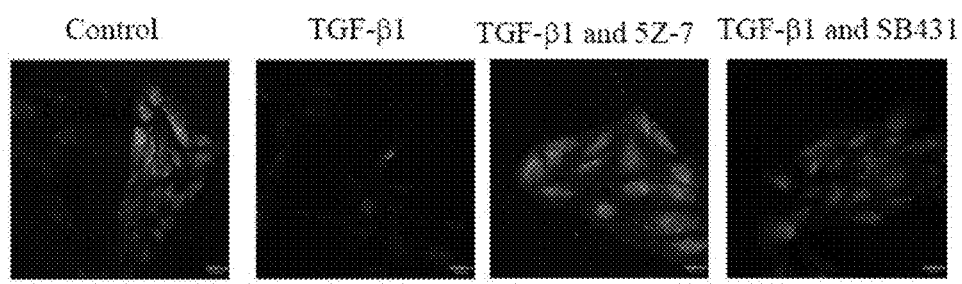

A recent publication has shown that down-regulation of the cell-cell adhesion protein E-cadherin, was considered a hallmark of EMT in RPE cells (Tamiya et al., *Invest Ophthalmol Vis Sci* 2010, 51:2755-2763). To investigate the participation of TAK1 in the regulation of E-cadherin, we again treated RPE cells with 5Z-7-oxozeaenol or SB431542 prior to TGF-β1 stimulation and immunostained the cells with anti-E-cadherin antibody. The result demonstrates that TAK1 is indeed involved in the regulation of E-cadherin expression (FIG. 3C). Control RPE cells express high levels of E-cadherin that almost completely disappear upon TGF-β1 addition. Inhibition of TAK1 reverses the effect of TGF-β1, allowing normal E-cadherin expression and thus maintaining the naive form of the RPE cells as in the control (FIG. 3C).

Example 3: TAK1 Regulates TGF-β Signaling in RPE Cells

The results shown in Example 2 indicated that inhibition of TAK1 reduced the expression of α-SMA and cell migration. These processes are known to be regulated in RPE cells by the TGF-β1 signaling through Smad2/3 (Mu Y et al., *Cell Tissue Res* 2011, 347:11-20). This example explores whether TAK1 inhibition would have an effect on the phosphorylation of Smad2/3.

Figure 4A:
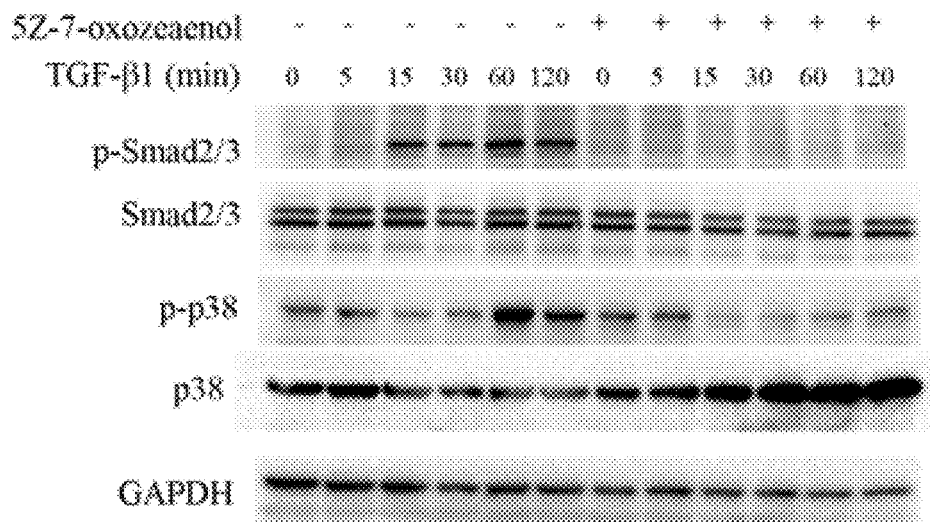
FIG. 4A-4C: Inhibition of TAK1 abolishes the activation of TGF-β cascades.
Figure 4B:
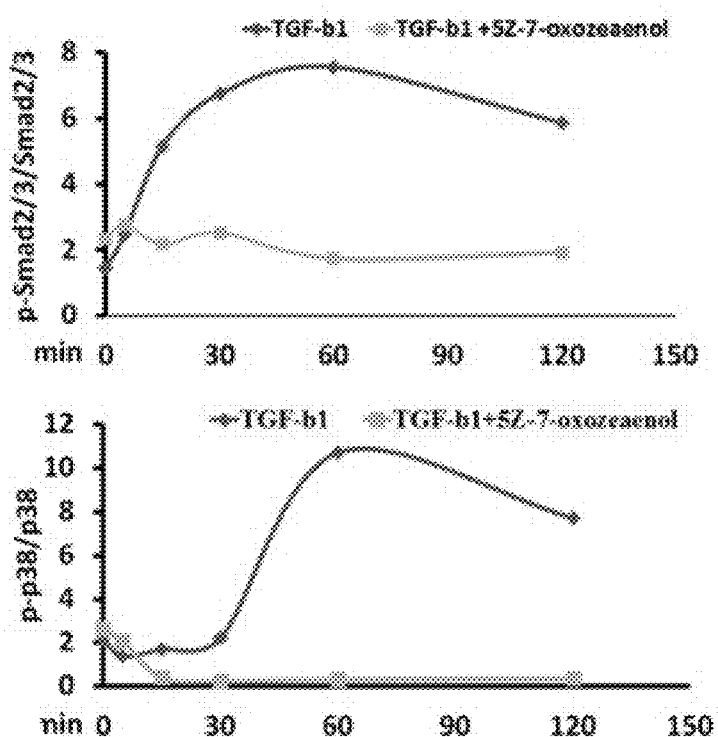
Figure 4C:
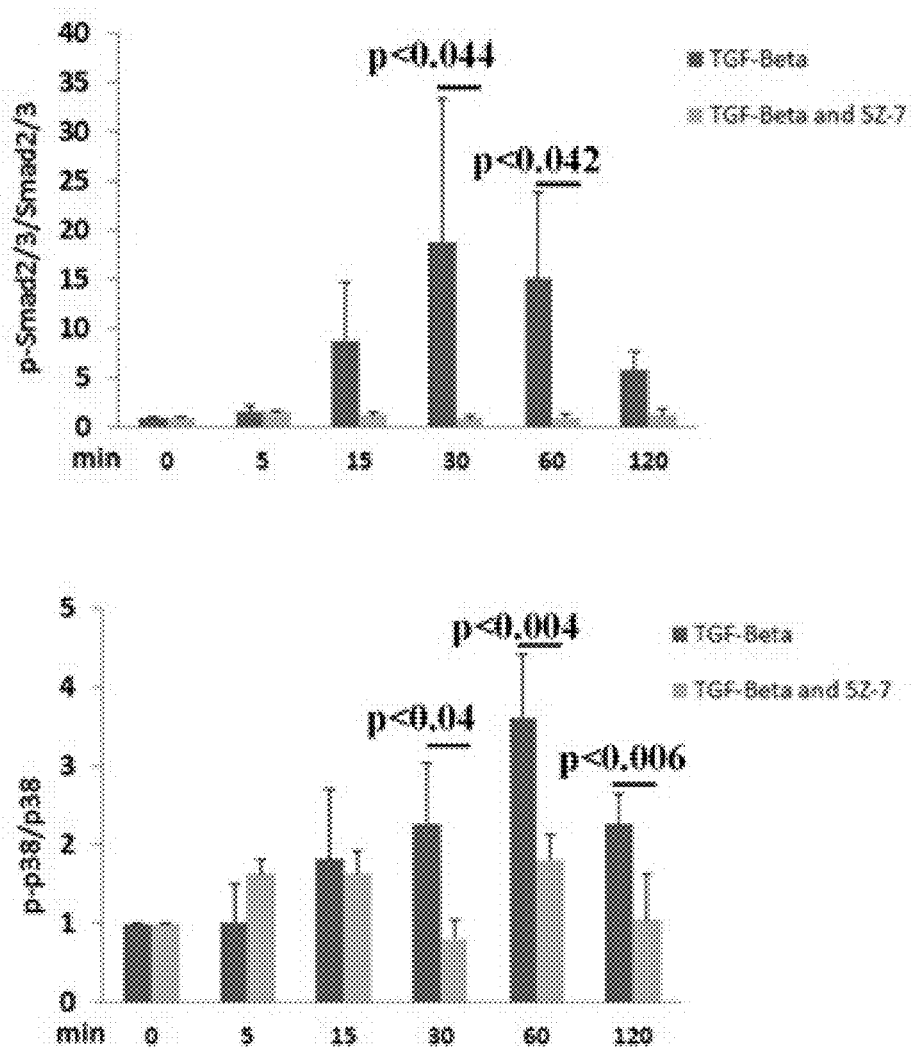

RPE cells were treated with or without 5Z-7-oxozeaenol followed by TGF-β1 treatment and Smad2/3 phosphorylation patterns were examined by immuno-blots. We observed that in TGF-β1 treated cells, phospho-Smad2/3 immediately increased and reached maximal activation at 60 minutes (FIG. 4A). In contrast, in the cells that were pre-treated with 5Z-7-oxozeaenol, Smad2/3 activation was barely detectable. Calculating the ratio of phospho-Smad2/3 to total Smad2/3 at each time point clearly demonstrated that inhibition of TAK1 activity abolished Smad2/3 activation in TGF-β1-stimulated RPE cells (FIG. 4B). Examination of the phosphorylation of p38, belonging to the non-canonical pathway of TGF-β1, revealed similar results to those obtained in the Smad2/3 signaling. Upon TGF-β1 stimulation, the phosphorylation of p38 increased, reaching a peak at 60 min (FIGS. 4A and C). In contrast, applying TAK1 inhibitor abolished p38 activation upon TGF-β1 stimulation (FIG. 4C). These results demonstrate that inhibition of TAK1 halts both the canonical and non-canonical cascades of TGF-β1.

Example 4: TAK1 Activity is Essential for EMT of the RPE Cells

Figure 5A:
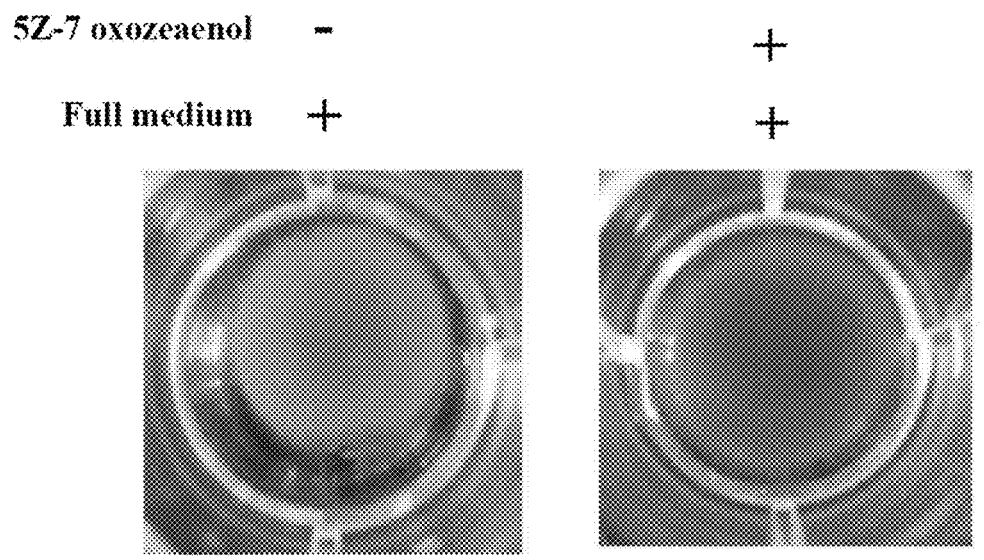
FIGS. 5A and 5B show that TAK1 is a general regulator of the EMT process in RPE cells.
Figure 5B:
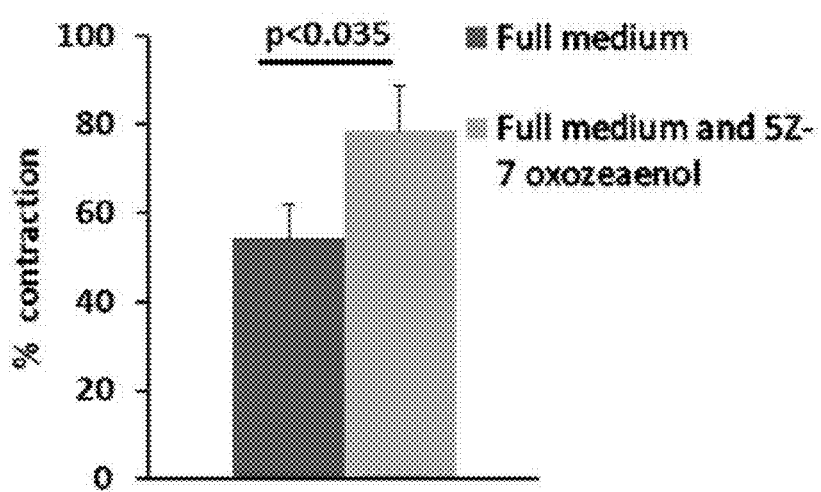
Figure 9:
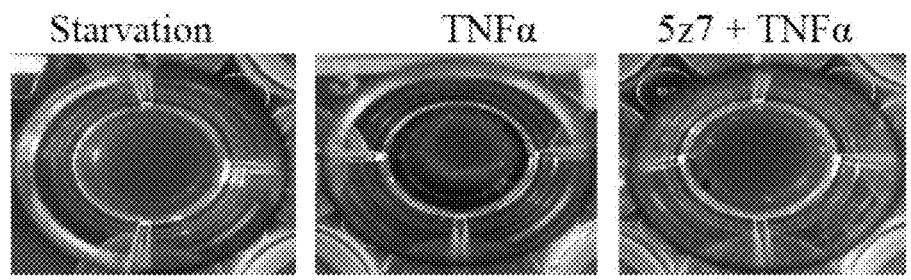
FIG. 9: TAK1 regulates RPE cells contraction upon TNFα stimulation. TAK1 inhibitor reduced the contraction of collagen caused by TNFα in RPE cells. RPE cells were seeded in collagen lattices in serum starvation medium. The cells were pretreated with 1 μM 5Z-7 or 1 hour before adding 50 ng/ml TNFα. Lattice were photo-documented after 72 hours and measured using ImajeJ software.

The transition of RPE cells to myofibroblasts is characterized, among other aspects, by increased contractile activity (Umazume et al., *Invest Ophthalmol Vis Sci* 2013, 54:1150-1159; Sakamoto et al., *Curr Eye Res* 1994, 13:451-459; West-Mays et al., *Int J Biochem Cell Biol* 2006, 38:1625-1631; Ma et al., *Clinical & experimental ophthalmology* 2012, 40:e76-86). To examine whether TAK1 is a general regulator of the EMT process affecting cell contractility, floating collagen matrix contraction assay was performed. The test was carried out in full serum with or without TAK1 inhibitor (FIGS. 5A and 5B). While in the control cells significant contraction was observed after 24 hours, reaching 50% of the initial size, TAK1 inhibition impaired the capacity of the cells to contract. The collagen lattice remained nearly 80% from the initial size (FIGS. 5A and B). Similarly, treatment of RPE cells with a TAK1 inhibitor following EMT stimulation by TNFα significantly reduced collagen contraction (FIG. 9).

Example 5: Aberrant Activity of TAK1 in Human Pathologic Retina

The previous examples demonstrate that TAK1 plays a significant role is EMT in RPE cells. This example shows that TAK1 is aberrantly expressed in human pathologic retina. To determine the expression pattern of TAK1 in retina tissue of normal and pathologic specimens. As shown in FIGS. 6A-6D and 7A-7D, TAK1 is aberrantly expressed in retinal tissues from blind eyes.

Example 6: 5Z-7-Oxozeaenol for Treatment of PVR

The above examples demonstrate that the TAK1 inhibitor 5Z-7-oxozeaenol can inhibit the causative physiological pathways of PVR. Accordingly TAK1 inhibitors, such as 5Z-7-oxozeaenol, and derivatives thereof, can be used as pharmaceutical agents to treat subjects with retinal trauma (such as RD), who are at risk of developing PVR.

A subject with RD is treated upon diagnosis with a therapeutically effective amount of a pharmaceutical composition that includes 5Z-7-oxozeaenol, or a derivative thereof, as the active ingredient. Such subjects can be treated with eye drops to administer the pharmaceutical composition either before and/or after surgery for treatment of the RD. Success of the treatment can be measured by inhibition or prevention of the fibrosis and scarring associated with PVR, and by improved outcomes of RD-treatment surgery.

Example 7: TGF-β1 Up-Regulates Smad 2/3 and p38 Activation in Hepatic Cells Via TAK1 Activity This example shows that TAK1 plays a similar role in hepatic cells as in retinal cells, and that its inhibition can inhibit the phosphorylation cascade involved in hepatic EMT.

Figure 10:
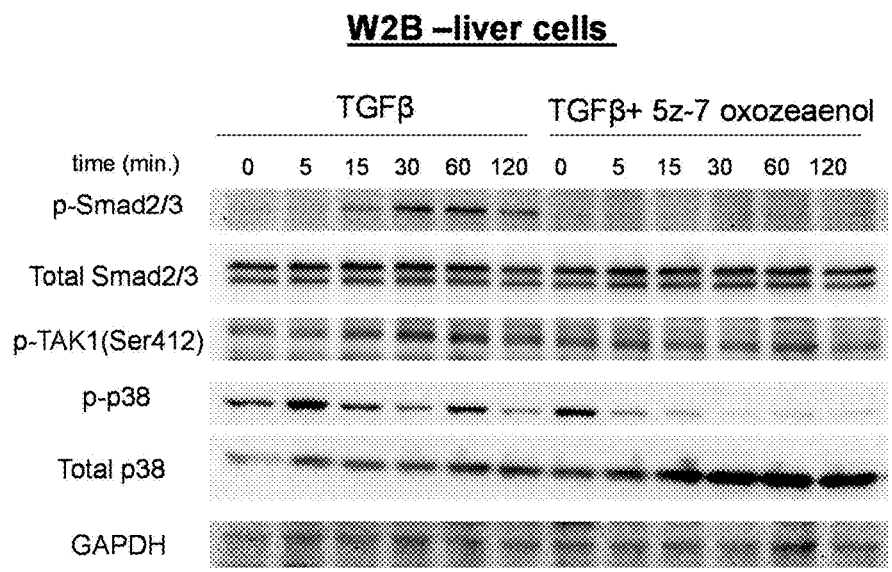
FIG. 10: Inhibition of TAK1 abolishes the activation of TGF-β cascades in liver cells. TGF-β1 up-regulates-Smad 2/3 and p38 activation and E-cadherin expression via TAK1 activity in hepatic cells. W2B liver hepatocytes cells were treated with or without 5Z-7-oxozeaenol followed by TGF-β treatment and Smad2/3 and p38 phosphorylation patterns were examined by immuno-blots.

W2b liver hepatocytes cells were treated with or without 5Z-7-oxozeaenol (1 µM) for 1 hour followed by TGF-β treatment (2.5 ng/ml) for the indicated times. Smad2/3 and p38 phosphorylation patterns were examined by immuno-blots as described above. It was observed that in TGF-β1 treated cells, phospho-Smad2/3 immediately increased and reached maximal activation at 60 minutes post-treatment (FIG. 10). Conversely, in cells that were pre-treated with 5Z-7-oxozeaenol, Smad2/3 and p38 activation was barely detectable. Thus demonstrating that inhibition of TAK1 abolish the activation of the signal transduction underlying fibrosis.

Example 8: 5Z-7-oxozeaenol Inhibition of TAK1 in Colon, Lung, and Aortic Cells

The previous examples show the inhibition of fibrosis-promoting pathways in retinal and hepatic cells. This example demonstrates that the TAK1-mediated pathway occurs similarly in colon, lung, and aortic cells.

Figure 11:
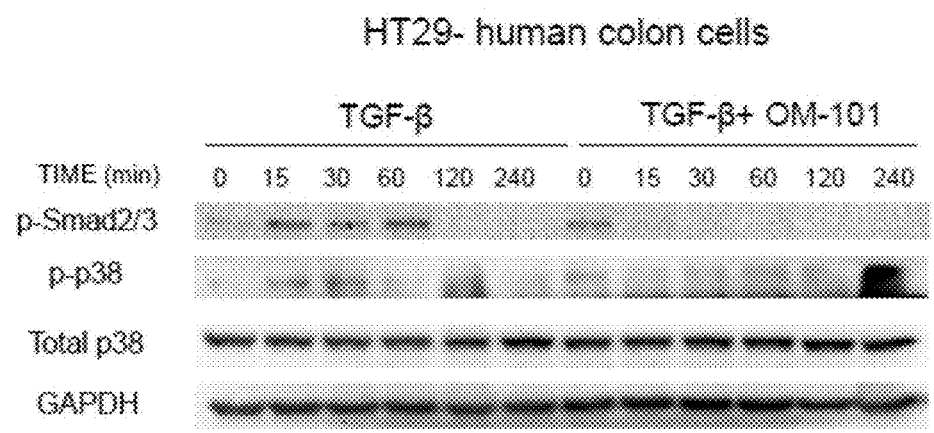
FIG. 11. Inhibition of TAK1 abolishes the activation of TGF-β cascades in colon cells. TGF-β1 up-regulates-Smad 2/3 and p38 activation via TAK1 activity in colon cells. HT29 Human colon cells were treated with or without 5Z-7-oxozeaenol followed by TGF-β treatment. Smad2/3 and p38 phosphorylation patterns were examined by immuno-blots.
Figure 12:
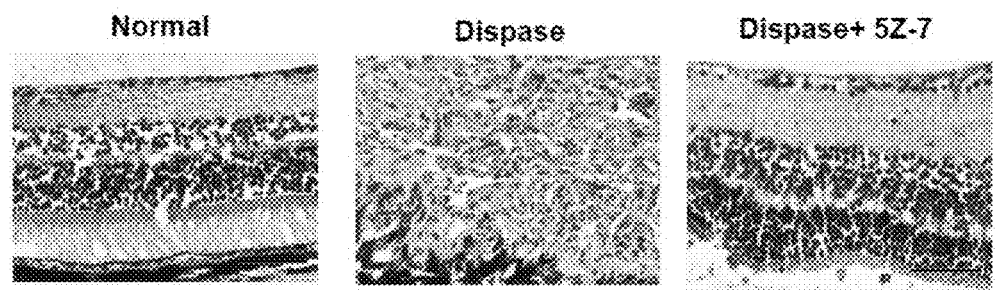
FIG. 12 shows the results of an experiment wherein 7-8 week old c57Black mice were treated or left untreated with dispase to generate PVR. 96 hour post-treatment, the mice were further treated with 5Z-7-oxozeaenol left untreated, and 96 hours later, mice were sacrificed, eyes were enucleated and stained with hematoxylin and eosin (H&E). The left panel shows normal retinal tissue. As shown in the middle panel, dispase caused PVR, manifested by loss of normal cellular architecture of the retina, presence of numerous inflammatory cells and presence of RPE cells throughout all retinal layers compared to the control (left panel). As shown in the right panel, treatment with 5Z-7-oxozeaenol maintained the normal retinal structure and prevented the development of the fibrotic response.

HT29 Human colon cells were treated as in the previous examples with or without 5Z-7-oxozeaenol, followed by TGF-β treatment. Inhibition of TAK1 was assayed by observation of Smad2/3 and p38 phosphorylation patterns by immuno-blots. As shown in FIG. 11, Smad2/3 and p38 phosphorylation was significantly inhibited in the 5Z-7-treated cells in comparison to the untreated cells.

Figure 14:
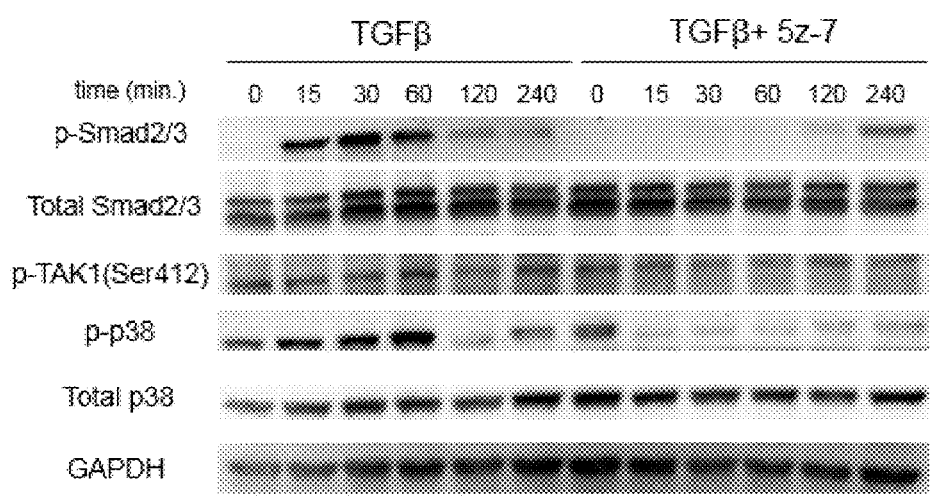
FIG. 14: Inhibition of TAK1 by 5z-7 abolishes the activation of TGF-β cascades in epithelial lung cells: Serum-starved A549 cells were pretreated with or without with 5Z-7-oxozeaenol (1 μM) for 1 hour and then with TGF-β (2.5 ng/ml) for the indicated times. Total protein extracts were analyzed by western blot using the indicated antibodies. The blot shows a representative result of four independent experiments. As can be seen, inhibition of TAK1 abolishes the fibrotic affect stimulated by TGF-β.
Figure 15:
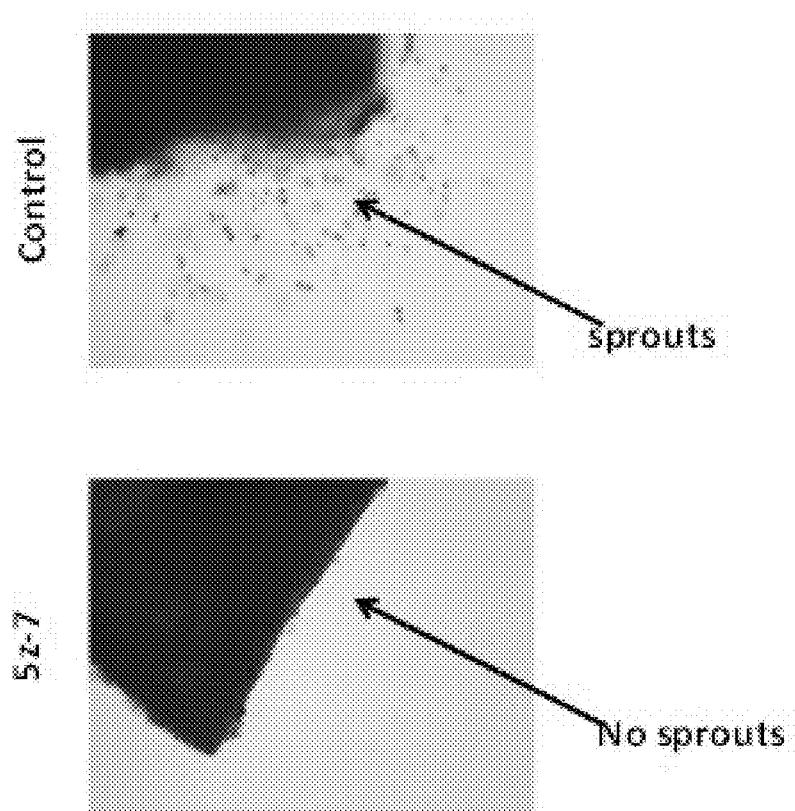
FIG. 15: TAK1 regulates the fibrotic switch in aortic injury ex vivo. aortic ring explants were seeded in Matrigel with or without 5z-7 (1 µM) for 8 days and then photo-documented. The photographs shown are representative from one of three independent experiments (N=9). As can been in the control aortic ring explants there is growth of sprouts due to the injury/fibrotic process. In contrast, employing 5z-7 abolish the fibrotic effect.

Similarly, A549 lung cells were pretreated with or without with 5Z-7-oxozeaenol (1 µM) for 1 hour and then with TGF-β (2.5 ng/ml). Total protein extracts were analyzed by western blot as in above, and the results are shown in FIG. 14. As can be seen, inhibition of TAK1 abolishes the fibrotic affect in lung cells that is stimulated by TGF-β.

Additionally, using the aortic ring assay (Baker et al., *Nature Protocols*, 7:89-104, 2012), treatment of aortic tissue explants with the TAK1 inhibitor 5z-7 can abolish the fibrotic effect resultant from the injury process.

Taken together with observations of the effect of TAK1 and its inhibition on ocular and hepatic cells, these observations indicate that the TAK1 fibrosis promoting pathway described herein is occurring and can be inhibited in a wide variety of tissue types.

Example 9: In Vivo Inhibition of PVR Development by TAK1 Inhibition

This example shows that in vivo treatment of rodents with a TAK1 inhibitor can inhibit the development of PVR.

7-8 week old c57Black mice were treated or left untreated with dispase to generate PVR in the mice. 96 hour post-treatment, the mice were treated with 5Z-7-oxozeaenol or left untreated, and 96 hour later, mice were sacrificed, eye were encapsulated and stained with hematoxylin and eosin (H&E).

As can be seen in FIG. 12, 5Z-7-oxozeaenol treatment prevents the development of the fibrotic response, and maintains the normal retinal structure.

Example 10: In Vivo Inhibition of Colitis by TAK1 Inhibition

This example shows that in vivo treatment of rodents with a TAK1 inhibitor can inhibit the development of the fibrotic effect associated with Colitis.

Figure 13:
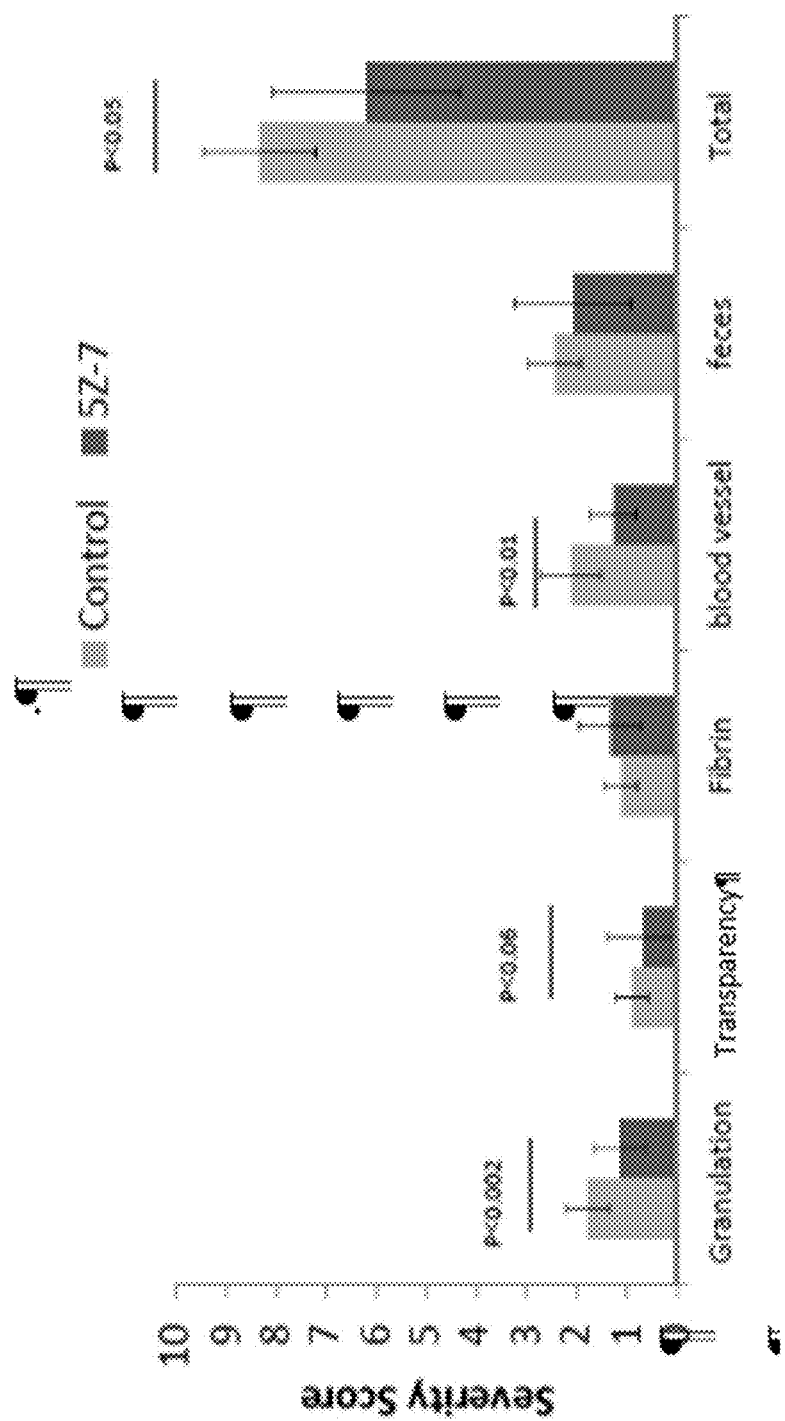
FIG. 13 shows that 5Z-7 reduces the fibrotic effect during colitis development in mice. C57black mice were treated with dextran sodium sulfate (DSS)-S 1.5% diluted in water for eight days and with or without 5Z-7 (1 uM) was IP injected total 180 ng for each animal Daily. After eight days the mice underwent evaluation to detect abnormalities in the Colom structure. N=14 mice for each group, Student T-test was used to determine the p value. The chart in FIG. 13 compares known markers that are considered as the main morphological phenotype for colitis. Each marker was given a score form 1-5 (5 being the most severe), with the total score demonstrating the severity of pathology.

C57black mice were treated with dextran sodium sulfate (DSS)-S 1.5% diluted in water for eight days and with or without 5Z-7 (1 uM) IP injected total 180 ng for each animal daily. After eight days the mice underwent evaluation to detect abnormalities in the colon structure. N=14 mice for each group, Student T-test was used to determine the p value. as can be seen in the chart shown in FIG. 13. In mice treated with DSS all markers of fibrosis such as: granulation, Transparency, fibrin and blood vessels were elevated by the DSS. In contrast, treatment of 5z-7 during reduce the fibrotic markers found upon DSS treatment.

Example 11: 5Z-7-Oxozeaenol for Treatment of Liver Fibrosis

The above examples demonstrate that the TAK1 inhibitor 5Z-7-oxozeaenol can inhibit the causative physiological pathways of liver fibrosis. Accordingly TAK1 inhibitors, such as 5Z-7-oxozeaenol, and functional derivatives thereof, can be used as pharmaceutical agents to treat subjects with liver trauma (such as inflammation), who are at risk of developing fibrosis.

A subject with liver inflammation is treated upon diagnosis with a therapeutically effective amount of a pharmaceutical composition that includes 5Z-7-oxozeaenol, or a derivative thereof, as the active ingredient. Success of the treatment can be measured by inhibition or prevention of the fibrosis and scarring associated with liver fibrosis, and by prevention of cirrhosis development.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for treatment of proliferative vitreoretinopathy (PVR), in a subject, comprising:
    administering to a subject in need thereof, a therapeutically effective amount of an inhibitor of at least one of the activation or kinase activity of transforming growth factor β activated kinase 1 (TAK-1),
    wherein the inhibitor is 5Z-7 oxozeaenol,
thereby treating the PVR.

2. The method of claim 1, wherein the inhibitor is administered to the subject after retinal detachment.

3. The method of claim 1, wherein the inhibitor is administered to the subject prior to, during, or after surgery for treatment of retinal detachment.

* * * * *